(12) United States Patent
Barry et al.

(10) Patent No.: US 6,663,906 B2
(45) Date of Patent: Dec. 16, 2003

(54) EXPRESSION OF FRUCTOSE 1,6 BISPHOSPHATE ALDOLASE IN TRANSGENIC PLANTS

(75) Inventors: Gerard F. Barry, St. Louis, MO (US); Nordine Cheikh, Manchester, MO (US); Ganesh M. Kishore, Creve Coeur, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 10/164,204

(22) Filed: Jun. 6, 2002

(65) Prior Publication Data

US 2003/0126641 A1 Jul. 3, 2003

Related U.S. Application Data

(62) Division of application No. 09/098,219, filed on Jun. 16, 1998, now Pat. No. 6,441,277.
(60) Provisional application No. 60/049,955, filed on Jun. 17, 1997.

(51) Int. Cl.[7] .......................... C12N 15/82; C12N 5/04; C12N 15/00; A01N 5/00; A01N 5/10
(52) U.S. Cl. ...................................... 426/438
(58) Field of Search ....................... 435/232; 800/317.2, 800/298; 426/637, 438, 560

(56) References Cited

FOREIGN PATENT DOCUMENTS

| WO | 90/10076 | 9/1990 | ........... C12N/15/82 |
|---|---|---|---|
| WO | 91/19806 | 12/1991 | ........... C12N/15/82 |
| WO | 96/21737 | 7/1996 | ........... C12N/15/55 |
| WO | 96/24679 | 8/1996 | ........... C12N/15/82 |

OTHER PUBLICATIONS

Alefounder et al. (1989) "Cloning, sequence analysis and over–expression of the gene for the Class II fructose 1,6 biphosphate aldolase of *Escherichia coli*" *Biochem. J.* 257:529–534.

Baldwin et al. (1978) "Purification and characterization of the Class II D–fructose 1,6 biphosphate aldolase from *Escherichia coli* (Crooke's Strain)" *Biochem. J.* 169:633–641.

Sonnewald et al. (1994) "Manipulation of sink–source relations in transgenic plants" *Plant Cell and Environment* 17:649–658.

Juan et al. "Over–expression of cytosolic fructose 1,6 biphosphatase in transgenic tobacco plants" *Plant Physiol.* 105(1):118 (1994).

Kossman et al. (1994) "Reduction of the chloroplastic fructose 1,6 biphosphatase in transgenic potato plants impairs photosynthesis and plant growth" *The Plant Journal* 6(5):637–650.

Scott et al. "Carbon metalbolism in leaves of transgenic tobacco (*Nicotiana tabacum* L.) containing elevated fructose 2, 6 biphosphate levels" *The Plant Journal* 7(3):461–469. (1995).

Scott et al. (1995) "Influence of elevated fructose 2, 6 biphosphate levels on starch mobilization in transgenic tobacco leaves in the dark" *Plant Physiol.* 108:1569–1577.

Zrenner et al. (1996) "Reduction of the cytosolic fructose 1, 6 biphosphatase in transgenic potato plants limits photosynthesis sucrose biosynthesis with no impact on plant growth and tuber yield" *The plant Journal* 9(5):671–681.

Newell et al. (1991) "*Agrobacterium*–mediated transformation of *Solanum tuberosum* L. cv. 'Russet–Burbank'" *Plant Cell Report* 10:30–34.

Smith et al. (1988) "Antisense RNA inhibition of polygalacturonase gene expession in transgenic tomatoes" *Nature* 334(25):724–726.

Alefounder et al. (1989) Accession No.: X14436 X14682.

Hidaka et al. (1990) "Nucleotide sequence of the rice cytoplasmic aldolase cDNA" *Nucleic Acid Res.* 18(13):3991–3999.

*Primary Examiner*—Keith Hendricks
(74) *Attorney, Agent, or Firm*—Thomas P. McBride; Howrey Simon Arnold & White, LLP

(57) ABSTRACT

Fructose-1,6-bisphosphate aldolase (FDA) is an enzyme reversibly catalyzing the reaction converting triosephosphate into fructose-1,6-bisphosphate. In the leaf, this enzyme is located in the chloroplast (starch synthesis) and the cytosol (sucrose biosynthesis). Transgenic plants were generated that express the *E. coli* fda gene in the chloroplast to improve plant yield by increasing leaf starch biosynthetic ability in particular and sucrose production in general. Leaves from plants expressing the fda transgene showed a significantly higher starch accumulation, as compared to control plants expressing the null vector, particularly early in the photoperiod, but had lower leaf sucrose. Transgenic plants also had a significantly higher root mass. Furthermore, transgenic potatoes expressing fda exhibited improved uniformity of solids.

6 Claims, 11 Drawing Sheets

TGCAACTTGAAGTATGACGAGTATAAGGCCCGACGATACAGGACAAGAGACATGTCTAAG
                                                      MetSerLys

ATTTTTGATTTCGTAAAACCTGGCGTAATCACTGGTGATGACGTACAGAAAGTTTTCCAG
IlePheAspPheValLysProGlyValIleThrGlyAspAspValGlnLysValPheGln

GTAGCAAAAGAAAACAACTTCGCACTGCCAGCAGTAAACTGCGTCGGTACTGACTCCATC
ValAlaLysGluAsnAsnPheAlaLeuProAlaValAsnCysValGlyThrAspSerIle

AACGCCGTACTGGAAACCGCTGCTAAAGTTAAAGCGCCGGTTATCGTTCAGTTCTCCAAC
AsnAlaValLeuGluThrAlaAlaLysValLysAlaProValIleValGlnPheSerAsn

GGTGGTGCTTCCTTTATCGCTGGTAAAGGCGTGAAATCTGACGTTCCGCAGGGTGCTGCT
GlyGlyAlaSerPheIleAlaGlyLysGlyValLysSerAspValProGlnGlyAlaAla

ATCCTGGGCGCGATCTCTGGTGCGCATCACGTTCACCAGATGGCTGAACATTATGGTGTT
IleLeuGlyAlaIleSerGlyAlaHisHisValHisGlnMetAlaGluHisTyrGlyVal

CCGGTTATCCTGCACACTGACCACTGCGCGAAGAAACTGCTGCCGTGGATCGACGGTCTG
ProValIleLeuHisThrAspHisCysAlaLysLysLeuLeuProTrpIleAspGlyLeu

TTGGACGCGGGTGAAAAACACTTCGCAGCTACCGGTAAGCCGCTGTTCTCTTCTCACATG
LeuAspAlaGlyGluLysHisPheAlaAlaThrGlyLysProLeuPheSerSerHisMet

ATCGACCTGTCTGAAGAATCTCTGCAAGAGAACATCGAAATCTGCTCTAAATACCTGGAG
IleAspLeuSerGluGluSerLeuGlnGluAsnIleGluIleCysSerLysTyrLeuGlu

CGCATGTCCAAAATCGGCATGACTCTGGAAATCGAACTGGGTTGCACCGGTGGTGAAGAA
ArgMetSerLysIleGlyMetThrLeuGluIleGluLeuGlyCysThrGlyGlyGluGlu

GACGGCGTGGACAACAGCCACATGGACGCTTCTGCACTGTACACCCAGCCGGAAGACGTT
AspGlyValAspAsnSerHisMetAspAlaSerAlaLeuTyrThrGlnProGluAspVal

GATTACGCATACACCGAACTGAGCAAAATCAGCCCGCGTTTCACCATCGCAGCGTCCTTC
AspTyrAlaTyrThrGluLeuSerLysIleSerProArgPheThrIleAlaAlaSerPhe

FIG. 1A

```
GGTAACGTACACGGTGTTTACAAGCCGGGTAACGTGGTTCTGACTCCGACCATCCTGCGT
GlyAsnValHisGlyValTyrLysProGlyAsnValValLeuThrProThrIleLeuArg

GATTCTCAGGAATATGTTTCCAAGAAACACAACCTGCCGCACAACAGCCTGAACTTCGTA
AspSerGlnGluTyrValSerLysLysHisAsnLeuProHisAsnSerLeuAsnPheVal

TTCCACGGTGGTTCCGGTTCTACTGCTCAGGAAATCAAAGACTCCGTAAGCTACGGCGTA
PheHisGlyGlySerGlySerThrAlaGlnGluIleLysAspSerValSerTyrGlyVal

GTAAAAATGAACATCGATACCGATACCCAATGGGCAACCTGGGAAGGCGTTCTGAACTAC
ValLysMetAsnIleAspThrAspThrGlnTrpAlaThrTrpGluGlyValLeuAsnTyr

TACAAAGCGAACGAAGCTTATCTGCAGGGTCAGCTGGGTAACCCGAAAGGCGAAGATCAG
TyrLysAlaAsnGluAlaTyrLeuGlnGlyGlnLeuGlyAsnProLysGlyGluAspGln

CCGAACAAGAAATACTACGATCCGCGCGTATGGCTGCGTGCCGGTCAGACTTCGATGATC
ProAsnLysLysTyrTyrAspProArgValTrpLeuArgAlaGlyGlnThrSerMetIle

GCTCGTCTGGAGAAAGCATTCCAGGAACTGAACGCGATCGACGTTCTGTAAGATATTCCT
AlaArgLeuGluLysAlaPheGlnGluLeuAsnAlaIleAspValLeuEnd

TTCTGCTTATCTCAAGGCCCGCTCTGCGGGTCTTTTTTTCG
```

FIG. 1B

```
                            SEQUENCE LISTING

<160> NUMBER OF SEQ ID NOS: 6

<210> SEQ ID NO 1
<211> LENGTH: 1080
<212> TYPE: DNA
<213> ORGANISM: E. coli

<400> SEQUENCE: 1
atgtctaaga ttttgattt cgtaaaacct ggcgtaatca ctggtgatga cgtacagaaa      60
gttttccagg tagcaaaaga aaacaacttc gcactgccag cagtaaactg cgtcggtact     120
gactccatca acgccgtact ggaaaccgct gctaaagtta aagcgccggt tatcgttcag     180
ttctccaacg gtggtgcttc ctttatcgct ggtaaaggcg tgaaatctga cgttccgcag     240
ggtgctgcta tcctgggcgc gatctctggt gcgcatcacg ttcaccagat ggctgaacat     300
tatggtgttc cggttatcct gcacactgac cactgcgcga agaaactgct gccgtggatc     360
gacggtctgt tggacgcggg tgaaaaacac ttcgcagcta ccggtaagcc gctgttctct     420
tctcacatga tcgacctgtc tgaagaatct ctgcaagaga acatcgaaat ctgctctaaa     480
tacctggagc gcatgtccaa aatcggcatg actctggaaa tcgaactggg ttgcaccggt     540
ggtgaagaag acgcgtgga caacagccac atggacgctt ctgcactgta cacccagccg     600
gaagacgttg attacgcata caccgaactg agcaaaatca gcccgcgttt caccatcgca     660
gcgtccttcg gtaacgtaca cggtgtttac aagccgggta acgtggttct gactccgacc     720
atcctgcgtg attctcagga atatgtttcc aagaaacaca acctgccgca caacagcctg     780
aacttcgtat tccacggtgg ttccggttct actgctcagg aaatcaaaga ctccgtaagc     840
tacggcgtag taaaaatgaa catcgatacc gatacccaat gggcaacctg ggaaggcgtt     900
ctgaactact acaaagcgaa cgaagcttat ctgcagggtc agctgggtaa cccgaaaggc     960
gaagatcagc cgaacaagaa atactacgat ccgcgcgtat ggctgcgtgc cggtcagact    1020
tcgatgatcg ctcgtctgga gaaagcattc caggaactga acgcgatcga cgttctgtaa    1080

<210> SEQ ID NO 2
<211> LENGTH: 359
<212> TYPE: PRT
<213> ORGANISM: E. coli

<400> SEQUENCE: 2

Met Ser Lys Ile Phe Asp Phe Val Lys Pro Gly Val Ile Thr Gly Asp
1               5                   10                  15

Asp Val Gln Lys Val Phe Gln Val Ala Lys Glu Asn Asn Phe Ala Leu
            20                  25                  30

Pro Ala Val Asn Cys Val Gly Thr Asp Ser Ile Asn Ala Val Leu Glu
        35                  40                  45

Thr Ala Lys Val Lys Ala Pro Val Ile Val Gln Phe Ser Asn Gly
    50                  55                  60

Gly Ala Ser Phe Ile Ala Gly Lys Gly Val Lys Ser Asp Val Pro Gln
65                  70                  75                  80

Gly Ala Ala Ile Leu Gly Ala Ile Ser Gly Ala His His Val His Gln
                85                  90                  95
```

```
Met Ala Glu His Tyr Gly Val Pro Val Ile Leu His Thr Asp His Cys
            100                 105                 110
Ala Lys Lys Leu Leu Pro Trp Ile Asp Gly Leu Leu Asp Ala Gly Glu
        115                 120                 125
Lys His Phe Ala Ala Thr Gly Lys Pro Leu Phe Ser Ser His Met Ile
    130                 135                 140
Asp Leu Ser Glu Glu Ser Leu Gln Glu Asn Ile Glu Ile Cys Ser Lys
145                 150                 155                 160
Tyr Leu Glu Arg Met Ser Lys Ile Gly Met Thr Leu Glu Ile Glu Leu
                165                 170                 175
Gly Cys Thr Gly Gly Glu Glu Asp Gly Val Asp Asn Ser His Met Asp
            180                 185                 190
Ala Ser Ala Leu Tyr Thr Gln Pro Glu Asp Val Asp Tyr Ala Tyr Thr
        195                 200                 205
Glu Leu Ser Lys Ile Ser Pro Arg Phe Thr Ile Ala Ala Ser Phe Gly
    210                 215                 220
Asn Val His Gly Val Tyr Lys Pro Gly Asn Val Val Leu Thr Pro Thr
225                 230                 235                 240
Ile Leu Arg Asp Ser Gln Glu Tyr Val Ser Lys Lys His Asn Leu Pro
                245                 250                 255
His Asn Ser Leu Asn Phe Val Phe His Gly Gly Ser Gly Ser Thr Ala
            260                 265                 270
Gln Glu Ile Lys Asp Ser Val Ser Tyr Gly Val Val Lys Met Asn Ile
        275                 280                 285
Asp Thr Asp Thr Gln Trp Ala Thr Trp Glu Gly Val Leu Asn Tyr Tyr
    290                 295                 300
Lys Ala Asn Glu Ala Tyr Leu Gln Gly Gln Leu Gly Asn Pro Lys Gly
305                 310                 315                 320
Glu Asp Gln Pro Asn Lys Lys Tyr Tyr Asp Pro Arg Val Trp Leu Arg
                325                 330                 335
Ala Gly Gln Thr Ser Met Ile Ala Arg Leu Glu Lys Ala Phe Gln Glu
            340                 345                 350
Leu Asn Ala Ile Asp Val Leu
        355

<210> SEQ ID NO 3
<211> LENGTH: 30
<212> TYPE: DNA
<213> ORGANISM: Artificial Sequence
<220> FEATURE:
<223> OTHER INFORMATION: Oligonucleotide

<400> SEQUENCE: 3
ggggccatgg ctaagatttt tgatttcgta                                    30

<210> SEQ ID NO 4
<211> LENGTH: 34
<212> TYPE: DNA
<213> ORGANISM: Artificial Sequence
<220> FEATURE:
<223> OTHER INFORMATION: Oligonucleotide

<400> SEQUENCE: 4
ccccgagctc ttacagaacg tcgatcgcgt tcag                               34

<210> SEQ ID NO 5
<211> LENGTH: 10846
```

<212> TYPE: DNA
<213> ORGANISM: Artificial Sequence
<220> FEATURE:
<223> OTHER INFORMATION: P-FMV/CTP1/fda/NOS3'

<400> SEQUENCE: 5

```
cgataagctt gatgtaattg gaggaagatc aaaattttca atccccattc ttcgattgct    60
tcaattgaag tttctccgat ggcgcaagtt agcagaatct gcaatggtgt gcagaaccca   120
tctcttatct ccaatctctc gaaatccagt caacgcaaat ctcccttatc ggtttctctg   180
aagacgcagc agcatccacg agcttatccg atttcgtcgt cgtggggatt gaagaagagt   240
gggatgacgt taattggctc tgagcttcgt cctcttaagg tcatgtcttc tgtttccacg   300
gcgtgcatgc ttcacggtgc aagcagccgt ccagcaactg ctcgtaagtc ctctggtctt   360
tctggaaccg tccgtattcc aggtgacaag tctatctccc acaggtcctt catgtttgga   420
ggtctcgcta gcggtgaaac tcgtatcacc ggtcttttgg aaggtgaaga tgttatcaac   480
actggtaagg ctatgcaagc tatgggtgcc agaatccgta aggaaggtga tcttggatc    540
attgatggtt tggtaacgg tggactcctt gctcctgagg ctcctctcga tttcggtaac   600
gctgcaactg gttgccgttt gactatgggt cttgttggtg tttacgattt cgatagcact   660
ttcattggtt acgcttctct cactaagcgt ccaatgggtc gtgtgttgaa cccacttcgc   720
gaaatgggtg tgcaggtgaa gtctgaagac ggtgatcgtc ttccagttac cttgcgtgga   780
ccaaagactc aacgccaat cacctacagg gtacctatgg cttccgctca agtgaagtcc    840
gctgttctgc ttgctggtct caacaccca gtatcacca ctgttatcga gccaatcatg      900
actcgtgacc acactgaaaa gatgcttcaa ggttttggtg ctaaccttac cgttgagact   960
gatgctgacg gtgtgcgtac catccgtctt gaaggtcgtg gtaagctcac cggtcaagtg  1020
attgatgttc caggtgatcc atcctctact gctttcccat tggttgctgc cttgcttgtt  1080
ccaggttccg acgtcaccat ccttaacgtt ttgatgaacc caacccgtac tggtctcatc  1140
ttgactctgc aggaaatggg tgccgacatc gaagtgatca acccacgtct tgctggtgga  1200
gaagacgtgg ctgacttgcg tgttcgttct tctactttga agggtgttac tgttccagaa  1260
gaccgtgctc cttctatgat cgacgagtat ccaattctcg ctgttgcagc tgcattcgct  1320
gaaggtgcta ccgttatgaa cggtttggaa gaactccgtg ttaaggaaag cgaccgtctt  1380
tctgctgtcg caaacggtct caagctcaac ggtgttgatt gcgatgaagg tgagacttct  1440
ctcgtcgtgc gtggtcgtcc tgacggtaag ggtctcggta acgcttctgg agcagctgtc  1500
gctacccacc tcgatcaccg tatcgctatg agcttcctcg ttatgggtct cgttctgaa   1560
aaccctgtta ctgttgatga tgctactatg atcgctacta gcttcccaga gttcatggat  1620
ttgatggctg gtcttggagc taagatcgaa ctctccgaca ctaaggctgc ttgatgagct  1680
caagaattcg agctcggtac cggatccagc tttcgttcgt atcatcggtt tcgacaacgt  1740
tcgtcaagtt caatgcatca gtttcattgc gcacacacca gaatcctact gagttcgagt  1800
attatggcat tgggaaaact gttttttcttg taccatttgt tgtgcttgta atttactgtg  1860
ttttttattc ggttttcgct atcgaactgt gaaatggaaa tggatggaga agagttaatg  1920
aatgatatgg tccttttgtt cattctcaaa ttaatattat ttgttttttc tcttatttgt  1980
tgtgtgttga atttgaaatt ataagagata tgcaaacatt ttgttttgag taaaaatgtg  2040
tcaaatcgtg gcctctaatg accgaagtta atatgaggag taaaacactt gtagttgtac  2100
cattatgctt attcactagg caacaaatat attttcagac ctagaaaagc tgcaaatgtt  2160
```

```
actgaataca agtatgtcct cttgtgtttt agacatttat gaactttcct ttatgtaatt    2220
ttccagaatc cttgtcagat tctaatcatt gctttataat tatagttata ctcatggatt    2280
tgtagttgag tatgaaaata ttttttaatg cattttatga cttgccaatt gattgacaac    2340
atgcatcaat cgacctgcag ccactcgaag cggccgcgtt caagcttgag ctcaggattt    2400
agcagcattc cagattgggt tcaatcaaca aggtacgagc catatcactt tattcaaatt    2460
ggtatcgcca aaaccaagaa ggaactccca tcctcaaagg tttgtaagga agaattctca    2520
gtccaaagcc tcaacaaggt cagggtacag agtctccaaa ccattagcca aaagctacag    2580
gagatcaatg aagaatcttc aatcaaagta aactactgtt ccagcacatg catcatggtc    2640
agtaagtttc agaaaaagac atccaccgaa gacttaaagt tagtgggcat cttttgaaagt    2700 aatcttgtca acatcgagca gctggcttgt ggggaccaga caaaaaagga atggtgcaga    2760
attgttaggc gcacctacca aaagcatctt tgcctttatt gcaaagataa agcagattcc    2820
tctagtacaa gtggggaaca aaataacgtg aaaagagct gtcctgacag cccactcact    2880
aatgcgtatg acgaacgcag tgacgaccac aaaagaattc cctctatata agaaggcatt    2940
cattcccatt tgaaggatca tcagatactg aaccaatcct tctagaagat ctccacaatg    3000
gcttcctcta tgctctcttc cgctactatg gttgcctctc cggctcaggc cactatggtc    3060
gctcctttca acgacttaa gtcctccgct gccttcccag ccacccgcaa ggctaacaac    3120
gacattactt ccatcacaag caacggcgga agagttaact gcatgcaggt gtggcctccg    3180
attggaaaga agagtttga gactctctct taccttcctg accttaccga ttccggtggt    3240
cgcgtcaact gcatgcaggc catggctaag attttttgatt tcgtaaaacc tggcgtaatc    3300
actggtgatg acgtacagaa agttttccag gtagcaaaag aaaacaactt cgcactgcca    3360
gcagtaaact gcgtcggtac tgactccatc aacgccgtac tggaaaccgc tgctaaagtt    3420
aaagcgccgg ttatcgttca gttctccaac ggtggtgctt cctttatcgc tggtaaaggc    3480
gtgaaatctg acgttccgca gggtgctgct atcctgggcg cgatctctgg tgcgcatcac    3540
gttcaccaga tggctgaaca ttatggtgtt ccggttatcc tgcacactga ccactgcgcg    3600
aagaaactgc tgccgtggat cgacggtctg ttggacgcgg gtgaaaaaca cttcgcagct    3660
accggtaagc cgctgttctc ttctcacatg atcgacctgt ctgaagaatc tctgcaagag    3720
aacatcgaaa tctgctctaa atacctggag cgcatgtcca aaatcggcat gactctggaa    3780
atcgaactgg gttgcaccgg tgtgaagaa gacggcgtgg acaacagcca catggacgct    3840
tctgcactgt acacccagcc ggaagacgtt gattacgcat acaccgaact gagcaaaatc    3900
agcccgcgtt tcaccatcgc agcgtccttc ggtaacgtac acggtgttta caagcccggt    3960
aacgtggttc tgactccgac catcctgcgt gattctcagg aatatgtttc caagaaacac    4020
aacctgccgc acaacagcct gaacttcgta ttccacggtg ttccggttc tactgctcag    4080 gaaatcaaag actccgtaag ctacggcgta gtaaaaatga acatcgatac cgataccccaa    4140 tgggcaacct gggaaggcgt tctgaactac tacaaagcga acgaagctta tctgcagggt    4200
cagctgggta acccgaaagg cgaagatcag ccgaacaaga atactacga tccgcgcgta    4260 tggctgcgtg ccggtcagac ttcgatgatc gctcgtctgg agaaagcatt ccaggaactg    4320
aacgcgatcg acgttctgta agagctcggt accggatcca attcccgatc gttcaaacat    4380
ttggcaataa agtttcttaa gattgaatcc tgttgccggt cttgcgatga ttatcatata    4440
atttctgttg aattacgtta agcatgtaat aattaacatg taatgcatga cgttatttat    4500
gagatgggtt tttatgatta gagtcccgca attatacatt taatacgcga tagaaaacaa    4560
```

```
aatatagcgc gcaaactagg ataaattatc gcgcgcggtg tcatctatgt tactagatcg    4620
gggatcgatc cccgggcggc cgccactcga gtggtggccg catcgatcgt gaagtttctc    4680
atctaagccc ccatttggac gtgaatgtag acacgtcgaa ataaagattt ccgaattaga    4740
ataatttgtt tattgctttc gcctataaat acgacggatc gtaatttgtc gttttatcaa    4800
aatgtacttt cattttataa taacgctgcg gacatctaca tttttgaatt gaaaaaaat    4860 tggtaattac tctttctttt tctccatatt gaccatcata ctcattgctg atccatgtag    4920
atttcccgga catgaagcca tttacaattg aatatatcct gccgccgctg ccgctttgca    4980
cccggtggag cttgcatgtt ggtttctacg cagaactgag ccggttaggc agataaattc    5040
cattgagaac tgagccatgt gcaccttccc cccaacacgg tgagcgacgg ggcaacggag    5100
tgatccacat gggactttc ctagcttggc tgccattttt ggggtgaggc cgttcgcgcg    5160
gggcgccagc tgggggggatg ggaggcccgc gttaccggga gggttcgaga aggggggca    5220 ccccccttcg gcgtgcgcgg tcacgcgcca gggcgcagcc ctggttaaaa acaaggttta    5280
taaatattgg tttaaaagca ggttaaaaga caggttagcg gtggccgaaa aacgggcgga    5340 aaccccttgca aatgctggat tttctgcctg tggacagccc ctcaaatgtc aataggtgcg    5400
cccctcatct gtcatcactc tgcccctcaa gtgtcaagga tcgcgcccct catctgtcag    5460
tagtcgcgcc cctcaagtgt caataccgca gggcacttat ccccaggctt gtccacatca    5520
tctgtgggaa actcgcgtaa aatcaggcgt tttcgccgat ttgcgaggct ggccagctcc    5580
acgtcgccgg ccgaaatcga gcctgcccct catctgtcaa cgccgcgccg ggtgagtcgg    5640
cccctcaagt gtcaacgtcc gcccctcatc tgtcagtgag ggccaagttt ccgcgtggt     5700 atccacaacg ccggcggccg gccgcggtgt ctcgcacacg gcttcgacgg cgtttctggc    5760
gcgtttgcag ggccatagac ggccgccagc ccagcggcga gggcaaccag cccggtgagc    5820
gtcggaaagg gtcgatcgac cgatgcccct gagagccttc aacccagtca gctccttccg    5880
gtgggcgcgg ggcatgacta tcgtcgccgc acttatgact gtcttcttta tcatgcaact    5940
cgtaggacag gtgccggcag cgctctgggt catttcggc gaggaccgct ttcgctggag    6000
cgcgacgatg atcggcctgt cgcttgcggt attcggaatc ttgcacgccc tcgctcaagc    6060
cttcgtcact ggtcccgcca ccaaacgttt cggcgagaag caggccatta tcgccggcat    6120
ggcggccgac gcgctgggct acgtcttgct ggcgttcgcg acgcgaggct ggatggcctt    6180
ccccattatg attcttctcg cttccggcgg catcgggatg cccgcgttgc aggccatgct    6240
gtccaggcag gtagatgacg accatcaggg acagcttcaa ggatcgctcg cggctcttac    6300
cagcctaact tcgatcactg gaccgctgat cgtcacggcg atttatgccg cctcggcgag    6360
cacatggaac gggttggcat ggattgtagg cgccgcccta taccttgtct gcctccccgc    6420
gttgcgtcgc ggtgcatgga gccgggccac ctcgacctga atggaagccg gcggcaccctc    6480 gctaacggat tcaccactcc aagaattgga gccaatcaat tcttgcggag aactgtgaat    6540
gcgcaaacca acccttggca gaacatatcc atcgcgtccg ccatctccag cagccgcacg    6600
cggcgcatct cgggcagcgt tgggtcctgg ccacgggtgc gcatgatcgt gctcctgtcg    6660
ttgaggaccc ggctaggctg gcggggttgc cttactggtt agcagaatga atcaccgata    6720
cgcgagcgaa cgtgaagcga ctgctgctgc aaaacgtctg cgacctgagc aacaacatga    6780
atggtcttcg gtttccgtgt ttcgtaaagt ctggaaacgc ggaagtcagc gccctgcacc    6840
attatgttcc ggatctgcat cgcaggatgc tgctggctac cctgtggaac acctacatct    6900
```

```
gtattaacga agcgctggca ttgaccctga gtgattttc  tctggtcccg ccgcatccat    6960
accgccagtt gtttaccctc acaacgttcc agtaaccggg catgttcatc atcagtaacc    7020
cgtatcgtga gcatcctctc tcgtttcatc ggtatcatta ccccatgaa  cagaaattcc    7080
cccttacacg gaggcatcaa gtgaccaaac aggaaaaaac cgcccttaac atggcccgct    7140
ttatcagaag ccagacatta acgcttctgg agaaactcaa cgagctggac gcggatgaac    7200
aggcagacat ctgtgaatcg cttcacgacc acgctgatga gctttaccgc agctgcctcg    7260
cgcgtttcgg tgatgacggt gaaaacctct gacacatgca gctcccggag acggtcacag    7320
cttgtctgta agcggatgcc gggagcagac aagcccgtca gggcgcgtca gcgggtgttg    7380
gcgggtgtcg gggcgcagcc atgacccagt cacgtagcga tagcggagtg tatactggct    7440
taactatgcg gcatcagagc agattgtact gagagtgcac catatgcggt gtgaaatacc    7500
gcacagatgc gtaaggagaa ataccgcat  caggcgctct ccgcttcct  cgctcactga    7560
ctcgctgcgc tcggtcgttc ggctgcggcg agcggtatca gctcactcaa aggcggtaat    7620
acggttatcc acagaatcag gggataacgc aggaaagaac atgtgagcaa aaggccagca    7680
aaaggccagg aaccgtaaaa aggccgcgtt gctggcgttt ttccataggc tccgccccc    7740
tgacgagcat cacaaaaatc gacgctcaag tcagaggtgg cgaaacccga caggactata    7800
aagataccag gcgtttcccc ctggaagctc cctcgtgcgc tctcctgttc cgaccctgcc    7860
gcttaccgga tacctgtccg cctttctccc ttcgggaagc gtggcgcttt ctcatagctc    7920
acgctgtagg tatctcagtt cggtgtaggt cgttcgctcc aagctgggct gtgtgcacga    7980
acccccccgtt cagcccgacc gctgcgcctt atccggtaac tatcgtcttg agtccaaccc    8040
ggtaagacac gacttatcgc cactggcagc agccactggt aacaggatta gcagagcgag    8100
gtatgtaggc ggtgctacag agttcttgaa gtggtggcct aactacggct acactagaag    8160
gacagtattt ggtatctgcg ctctgctgaa gccagttacc ttcggaaaaa gagttggtag    8220
ctcttgatcc ggcaaacaaa ccaccgctgg tagcggtggt ttttttgttt gcaagcagca    8280
gattacgcgc agaaaaaaag gatctcaaga agatcctttg atcttttcta cggggtctga    8340
cgctcagtgg aacgaaaact cacgttaagg gattttggtc atgagattat caaaaaggat    8400
cttcacctag atcctttta  attaaaaatg aagttttaaa tcaatctaaa gtatatatga    8460
gtaaacttgg tctgacagtt accaatgctt aatcagtgag gcacctatct cagcgatctg    8520
tctatttcgt tcatccatag ttgcctgact ccccgtcgtg tagataacta cgatacggga    8580
gggcttacca tctggcccca gtgctgcaat gataccgcga gacccacgct caccggctcc    8640
agatttatca gcaataaacc agccagccgg aagggccgag cgcagaagtg gtcctgcaac    8700
tttatccgcc tccatccagt ctattaattg ttgccgggaa gctagagtaa gtagttcgcc    8760
agttaatagt ttgcgcaacg ttgttgccat tgctgcaggt cgggagcaca ggatgacgcc    8820
taacaattca ttcaagccga caccgcttcg cggcgcggct taattcagga gttaaacatc    8880
atgagggaag cggtgatcgc cgaagtatcg actcaactat cagaggtagt tggcgtcatc    8940
gagcgccatc tcgaaccgac gttgctggcc gtacatttgt acggctccgc agtggatggc    9000
ggcctgaagc cacacagtga tattgatttg ctggttacgg tgaccgtaag gcttgatgaa    9060
acaacgcggc gagctttgat caacgacctt ttggaaactt cggcttcccc tggagagagc    9120
gagattctcc gcgctgtaga agtcaccatt gttgtgcacg acgacatcat tccgtggcgt    9180
tatccagcta agcgcgaact gcaatttgga gaatggcagc gcaatgacat tcttgcaggt    9240
atcttcgagc cagccacgat cgacattgat ctggctatct tgctgacaaa agcaagagaa    9300
```

```
catagcgttg ccttggtagg tccagcggcg gaggaactct tgatccggt tcctgaacag      9360 gatctatttg aggcgctaaa tgaaaccttc acgctatgga actcgccgcc cgactgggct      9420
ggcgatgagc gaaatgtagt gcttacgttg tcccgcattt ggtacagcgc agtaaccggc      9480
aaaatcgcgc cgaaggatgt cgctgccgac tgggcaatgg agcgcctgcc ggcccagtat      9540
cagcccgtca tacttgaagc taggcaggct tatcttggac aagaagatcg cttggcctcg      9600
cgcgcagatc agttggaaga atttgttcac tacgtgaaag gcgagatcac caaggtagtc      9660
ggcaaataat gtctaacaat tcgttcaagc cgacgccgct tcgcggcgcg gcttaactca      9720
agcgttagat gctgcaggca tcgtggtgtc acgctcgtcg tttggtatgg cttcattcag      9780
ctccggttcc caacgatcaa ggcgagttac atgatccccc atgttgtgca aaaagcggt      9840 tagctccttc ggtcctccga tcgaggattt ttcggcgctg cgctacgtcc gcaccgcgtt      9900
gagggatcaa gccacagcag cccactcgac ctctagccga cccagacgag ccaagggatc      9960
tttttggaat gctgctccgt cgtcaggctt tccgacgttt gggtggttga acagaagtca    10020
ttatcgtacg gaatgccaag cactcccgag gggaaccctg tggttggcat gcacatacaa    10080
atggacgaac ggataaacct tttcacgccc tttttaaatat ccgttattct aataaacgct    10140
cttttctctt aggtttaccc gccaatatat cctgtcaaac actgatagtt taaactgaag    10200
gcgggaaacg acaatctgat ccccatcaag cttgagctca ggatttagca gcattccaga    10260
ttgggttcaa tcaacaaggt acgagccata tcacttttatt caaattggta tcgccaaaac    10320
caagaaggaa ctcccatcct caaaggtttg taaggaagaa ttctcagtcc aaagcctcaa    10380
caaggtcagg gtacagagtc tccaaaccat tagccaaaag ctacaggaga tcaatgaaga    10440
atcttcaatc aaagtaaact actgttccag cacatgcatc atggtcagta agtttcagaa    10500
aaagacatcc accgaagact taagttagt gggcatcttt gaaagtaatc ttgtcaacat    10560
cgagcagctg gcttgtgggg accagacaaa aaaggaatgg tgcagaattg ttaggcgcac    10620
ctaccaaaag catctttgcc tttattgcaa agataaagca gattcctcta gtacaagtgg    10680
ggaacaaaat aacgtggaaa agagctgtcc tgacagccca ctcactaatg cgtatgacga    10740
acgcagtgac gaccacaaaa gaattccctc tatataagaa ggcattcatt cccatttgaa    10800
ggatcatcag atactgaacc aatccttcta gaagatctaa gcttat              10846
```

<210> SEQ ID NO 6
<211> LENGTH: 10900
<212> TYPE: DNA
<213> ORGANISM: Artificial Sequence
<220> FEATURE:
<223> OTHER INFORMATION: P-FMV/CTP2/fda/NO3'

<400> SEQUENCE: 6

```
cgataagctt gatgtaattg gaggaagatc aaaattttca atccccattc ttcgattgct        60
tcaattgaag tttctccgat ggcgcaagtt agcagaatct gcaatggtgt gcagaaccca       120
tctcttatct ccaatctctc gaatccagt caacgcaaat ctcccttatc ggtttctctg       180
aagacgcagc agcatccacg agcttatccg atttcgtcgt cgtggggatt gaagaagagt       240
gggatgacgt taattggctc tgagcttcgt cctcttaagg tcatgtcttc tgtttccacg       300
gcgtgcatgc ttcacggtgc aagcagccgt ccagcaactg ctcgtaagtc ctctggtctt       360
tctggaaccg tccgtattcc aggtgacaag tctatctccc acaggtcctt catgtttgga       420
ggtctcgcta gcggtgaaac tcgtatcacc ggtctttttgg aaggtgaaga tgttatcaac       480
```

-continued

| | | | | |
|---|---|---|---|---|
| actggtaagg | ctatgcaagc | tatgggtgcc | agaatccgta | aggaaggtga tacttggatc | 540 |
| attgatggtg | ttggtaacgg | tggactcctt | gctcctgagg | ctcctctcga tttcggtaac | 600 |
| gctgcaactg | gttgccgttt | gactatgggt | cttgttggtg | tttacgattt cgatagcact | 660 |
| ttcattggtg | acgcttctct | cactaagcgt | ccaatgggtc | gtgtgttgaa cccacttcgc | 720 |
| gaaatgggtg | tgcaggtgaa | gtctgaagac | ggtgatcgtc | ttccagttac cttgcgtgga | 780 |
| ccaaagactc | caacgccaat | cacctacagg | gtacctatgg | cttccgctca agtgaagtcc | 840 |
| gctgttctgc | ttgctggtct | caacacccca | ggtatcacca | ctgttatcga gccaatcatg | 900 |
| actcgtgacc | acactgaaaa | gatgcttcaa | ggttttggtg | ctaaccttac cgttgagact | 960 |
| gatgctgacg | tgtgcgtac | catccgtctt | gaaggtcgtg | gtaagctcac cggtcaagtg | 1020 |
| attgatgttc | caggtgatcc | atcctctact | gctttcccat | tggttgctgc cttgcttgtt | 1080 |
| ccaggttccg | acgtcaccat | ccttaacgtt | ttgatgaacc | caacccgtac tggtctcatc | 1140 |
| ttgactctgc | aggaaatggg | tgccgacatc | gaagtgatca | acccacgtct tgctggtgga | 1200 |
| gaagacgtgg | ctgacttgcg | tgttcgttct | tctactttga | agggtgttac tgttccagaa | 1260 |
| gaccgtgctc | cttctatgat | cgacgagtat | ccaattctcg | ctgttgcagc tgcattcgct | 1320 |
| gaaggtgcta | ccgttatgaa | cggtttggaa | gaactccgtg | ttaaggaaag cgaccgtctt | 1380 |
| tctgctgtcg | caaacggtct | caagctcaac | ggtgttgatt | gcgatgaagg tgagacttct | 1440 |
| ctcgtcgtgc | gtggtcgtcc | tgacggtaag | ggtctcggta | acgcttctgg agcagctgtc | 1500 |
| gctacccacc | tcgatcaccg | tatcgctatg | agcttcctcg | ttatgggtct cgtttctgaa | 1560 |
| aaccctgtta | ctgttgatga | tgctactatg | atcgctacta | gcttcccaga gttcatggat | 1620 |
| tgatggctg | gtcttggagc | taagatcgaa | ctctccgaca | ctaaggctgc ttgatgagct | 1680 |
| caagaattcg | agctcggtac | cggatccagc | tttcgttcgt | atcatcggtt tcgacaacgt | 1740 |
| tcgtcaagtt | caatgcatca | gtttcattgc | gcacacacca | gaatcctact gagttcgagt | 1800 |
| attatggcat | tgggaaaact | gttttttcttg | taccatttgt | tgtgcttgta atttactgtg | 1860 |
| tttttattc | ggttttcgct | atcgaactgt | gaaatgaaa | tggatggaga agagttaatg | 1920 |
| aatgatatgg | tcctttttgtt | cattctcaaa | ttaatattat | ttgttttttc tcttatttgt | 1980 |
| tgtgtgttga | atttgaaatt | ataagagata | tgcaaacatt | ttgttttgag taaaaatgtg | 2040 |
| tcaaatcgtg | gcctctaatg | accgaagtta | atatgaggag | taaaacactt gtagttgtac | 2100 |
| cattatgctt | attcactagg | caacaaatat | attttcagac | ctagaaaagc tgcaaatgtt | 2160 |
| actgaataca | agtatgtcct | cttgtgtttt | agacatttat | gaactttcct ttatgtaatt | 2220 |
| ttccagaatc | cttgtcagat | tctaatcatt | gcttttataat | tatagttata ctcatggatt | 2280 |
| tgtagttgag | tatgaaaata | tttttttaatg | cattttatga | cttgccaatt gattgacaac | 2340 |
| atgcatcaat | cgacctgcag | ccactcgaag | cggccgcgtt | caagcttgag ctcaggatttt | 2400 |
| agcagcattc | cagattgggt | tcaatcaaca | aggtacgagc | catatcactt tattcaaatt | 2460 |
| ggtatcgcca | aaaccaagaa | ggaactccca | tcctcaaagg | tttgtaagga agaattctca | 2520 |
| gtccaaagcc | tcaacaaggt | cagggtacag | agtctccaaa | ccattagcca aaagctacag | 2580 |
| gagatcaatg | aagaatcttc | aatcaaagta | aactactgtt | ccagcacatg catcatggtc | 2640 |
| agtaagtttc | agaaaaagac | atccaccgaa | gacttaaagt | tagtgggcat ctttgaaagt | 2700 |
| aatcttgtca | acatcgagca | gctggcttgt | ggggaccaga | caaaaaagga atggtgcaga | 2760 |
| attgttaggc | gcacctacca | aaagcatctt | tgcctttatt | gcaaagataa agcagattcc | 2820 |
| tctagtacaa | gtggggaaca | aaataacgtg | gaaagagct | gtcctgacag cccactcact | 2880 |

```
aatgcgtatg acgaacgcag tgacgaccac aaaagaattc cctctatata agaaggcatt    2940
cattcccatt tgaaggatca tcagatactg aaccaatcct tctagaagat ctaagcttat    3000
cgataagctt gatgtaattg gaggaagatc aaaattttca atccccattc ttcgattgct    3060
tcaattgaag tttctccgat ggcgcaagtt agcagaatct gcaatggtgt gcagaaccca    3120
tctcttatct ccaatctctc gaaatccagt caacgcaaat ctcccttatc ggtttctctg    3180
aagacgcagc agcatccacg agcttatccg atttcgtcgt cgtggggatt gaagaagagt    3240
gggatgacgt taattggctc tgagcttcgt cctcttaagg tcatgtcttc tgtttccacg    3300
gcgtgcatgc aggccatggc taagattttt gatttcgtaa aacctggcgt aatcactggt    3360
gatgacgtac agaaagtttt ccaggtagca aaagaaaaca cttcgcact gccagcagta     3420 aactgcgtcg gtactgactc catcaacgcc gtactggaaa ccgctgctaa agttaaagcg    3480
ccggttatcg ttcagttctc caacggtggt gcttccttta tcgctggtaa aggcgtgaaa    3540
tctgacgttc cgcagggtgc tgctatcctg ggcgcgatct ctggtgcgca tcacgttcac    3600
cagatggctg aacattatgg tgttccggtt atcctgcaca ctgaccactg cgcgaagaaa    3660
ctgctgccgt ggatcgacgg tctgttggac gcgggtgaaa acacttcgc agctaccggt     3720 aagccgctgt tctcttctca catgatcgac ctgtctgaag aatctctgca agagaacatc    3780
gaaatctgct ctaaatacct ggagcgcatg tccaaaatcg gcatgactct ggaaatcgaa    3840
ctgggttgca ccggtggtga agaagacggc gtggacaaca gccacatgga cgcttctgca    3900
ctgtacaccc agccggaaga cgttgattac gcatacaccg aactgagcaa aatcagcccg    3960
cgtttcacca tcgcagcgtc cttcggtaac gtacacggtg tttacaagcc gggtaacgtg    4020
gttctgactc cgaccatcct gcgtgattct caggaatatg tttccaagaa acacaacctg    4080
ccgcacaaca gcctgaactt cgtattccac ggtggttccg gttctactgc tcaggaaatc    4140
aaagactccg taagctacgg cgtagtaaaa atgaacatcg ataccgatac ccaatgggca    4200
acctgggaag gcgttctgaa ctactacaaa gcgaacgaag cttatctgca gggtcagctg    4260
ggtaacccga aggcgaaga tcagccgaac aagaaatact acgatccgcg cgtatggctg    4320
cgtgccggtc agacttcgat gatcgctcgt ctggagaaag cattccagga actgaacgcg    4380
atcgacgttc tgtaagagct cggtaccgga tccaattccc gatcgttcaa acatttggca    4440
ataaagtttc ttaagattga atcctgttgc cggtcttgcg atgattatca tataatttct    4500
gttgaattac gttaagcatg taataattaa catgtaatgc atgacgttat ttatgagatg    4560
ggtttttatg attagagtcc cgcaattata catttaatac gcgatagaaa acaaaatata    4620
gcgcgcaaac taggataaat tatcgcgcgc ggtgtcatct atgttactag atcggggatc    4680
gatccccggg cggccgccac tcgagtggtg gccgcatcga tcgtgaagtt tctcatctaa    4740
gcccccattt ggacgtgaat gtagacacgt cgaaataaag atttccgaat tagaataatt    4800
tgtttattgc tttcgcctat aaatacgacg gatcgtaatt tgtcgtttta tcaaaatgta    4860 cttttcatttt ataataacgc tgcggacatc tacattttg aattgaaaaa aaattggtaa    4920
ttactctttc ttttttctcca tattgaccat catactcatt gctgatccat gtagatttcc    4980
cggacatgaa gccatttaca attgaatata tcctgccgcc gctgccgctt tgcacccggt    5040
ggagcttgca tgttggtttc tacgcagaac tgagccggtt aggcagataa tttccattga    5100
gaactgagcc atgtgcacct tcccccaac acggtgagcg acgggcaac ggagtgatcc      5160 acatgggact tttcctagct tggctgccat ttttggggtg aggccgttcg cgcggggcgc    5220
```

-continued

```
cagctggggg gatgggaggc ccgcgttacc gggagggttc gagaaggggg ggcaccccccc    5280 ttcggcgtgc gcggtcacgc gccagggcgc agccctggtt aaaaacaagg tttataaata    5340
ttggtttaaa agcaggttaa aagacaggtt agcggtggcc gaaaaacggg cggaaaccct    5400
tgcaaatgct ggattttctg cctgtggaca gcccctcaaa tgtcaatagg tgcgcccctc    5460
atctgtcatc actctgcccc tcaagtgtca aggatcgcgc ccctcatctg tcagtagtcg    5520
cgcccctcaa gtgtcaatac cgcagggcac ttatcccag gcttgtccac atcatctgtg    5580
ggaaactcgc gtaaaatcag gcgttttcgc cgatttgcga ggctggccag ctccacgtcg    5640
ccggccgaaa tcgagcctgc ccctcatctg tcaacgccgc gccgggtgag tcggcccctc    5700
aagtgtcaac gtccgcccct catctgtcag tgagggccaa gttttccgcg tggtatccac    5760
aacgccggcg gccggccgcg gtgtctcgca cacggcttcg acggcgtttc tggcgcgttt    5820
gcagggccat agacggccgc cagcccagcg gcgagggcaa ccagcccggt gagcgtcgga    5880
aagggtcgat cgaccgatgc ccttgagagc cttcaaccca gtcagctcct tccggtgggc    5940
gcggggcatg actatcgtcg ccgcacttat gactgtcttc tttatcatgc aactcgtagg    6000
acaggtgccg gcagcgctct gggtcatttt cggcgaggac cgctttcgct ggagcgcgac    6060
gatgatcggc ctgtcgcttg cggtattcgg aatcttgcac gccctcgctc aagccttcgt    6120
cactggtccc gccaccaaac gtttcggcga aagcaggcc attatcgccg gcatggcggc    6180
cgacgcgctg ggctacgtct tgctggcgtt cgcgacgcga ggctggatgg ccttccccat    6240
tatgattctt ctcgcttccg gcggcatcgg gatgcccgcg ttgcaggcca tgctgtccag    6300
gcaggtagat gacgaccatc agggacagct tcaaggatcg ctcgcggctc ttaccagcct    6360
aacttcgatc actggaccgc tgatcgtcac ggcgatttat gccgcctcgg cgagcacatg    6420
gaacgggttg gcatggattg taggcgccgc cctataccttt gtctgcctcc ccgcgttgcg    6480
tcgcggtgca tggagccggg ccactcgac ctgaatggaa gccggcggca cctcgctaac    6540
ggattcacca ctccaagaat tggagccaat caattcttgc ggagaactgt gaatgcgcaa    6600
accaaccctt ggcagaacat atccatcgcg tccgccatct ccagcagccg cacgcggcgc    6660
atctcgggca gcgttgggtc ctggccacgg gtgcgcatga tcgtgctcct gtcgttgagg    6720
acccggctag gctggcgggg ttgccttact ggttagcaga atgaatcacc gatacgcgag    6780
cgaacgtgaa gcgactgctg ctgcaaaacg tctgcgacct gagcaacaac atgaatggtc    6840
ttcggtttcc gtgtttcgta aagtctggaa acgcggaagt cagcgccctg caccattatg    6900
ttccggatct gcatcgcagg atgctgctgg ctaccctgtg gaacacctac atctgtatta    6960
acgaagcgct ggcattgacc ctgagtgatt tttctctggt cccgccgcat ccataccgcc    7020
agttgtttac cctcacaacg ttccagtaac cgggcatgtt catcatcagt aacccgtatc    7080
gtgagcatcc tctctcgttt catcggtatc attaccccca tgaacagaaa ttccccctta    7140
cacggaggca tcaagtgacc aaacaggaaa aaaccgccct taacatggcc cgctttatca    7200
gaagccagac attaacgctt ctggagaaac tcaacgagct ggacgcggat gaacaggcag    7260
acatctgtga atcgcttcac gaccacgctg atgagcttta ccgcagctgc ctcgcgcgtt    7320
tcggtgatga cggtgaaaac ctctgacaca tgcagctccc ggagacgtc acagcttgtc    7380 tgtaagcgga tgccgggagc agacaagccc gtcagggcgc gtcagcgggt gttggcgggt    7440 gtcgggcgc agccatgacc cagtcacgta gcgatagcgg agtgtatact ggcttaacta    7500
tgcggcatca gagcagattg tactgagagt gcaccatatg cggtgtgaaa taccgcacag    7560
atgcgtaagg agaaaatacc gcatcaggcg ctcttccgct tcctcgctca ctgactcgct    7620
```

```
gcgctcggtc gttcggctgc ggcgagcggt atcagctcac tcaaaggcgg taatacggtt      7680
atccacagaa tcaggggata acgcaggaaa gaacatgtga gcaaaaggcc agcaaaaggc      7740
caggaaccgt aaaaaggccg cgttgctggc gttttccat aggctccgcc cccctgacga       7800
gcatcacaaa aatcgacgct caagtcagag gtggcgaaac ccgacaggac tataaagata      7860
ccaggcgttt ccccctggaa gctccctcgt gcgctctcct gttccgaccc tgccgcttac      7920
cggatacctg tccgcctttc tcccttcggg aagcgtggcg ctttctcata gctcacgctg      7980
taggtatctc agttcggtgt aggtcgttcg ctccaagctg ggctgtgtgc acgaaccccc      8040
cgttcagccc gaccgctgcg ccttatccgg taactatcgt cttgagtcca acccggtaag      8100
acacgactta tcgccactgg cagcagccac tggtaacagg attagcagag cgaggtatgt      8160
aggcggtgct acagagttct tgaagtggtg gcctaactac ggctacacta aaggacagt       8220 atttggtatc tgcgctctgc tgaagccagt taccttcgga aaaagagttg gtagctcttg      8280
atccggcaaa caaaccaccg ctggtagcgg tggttttttt gtttgcaagc agcagattac      8340
gcgcagaaaa aaaggatctc aagaagatcc tttgatcttt tctacggggt ctgacgctca      8400
gtggaacgaa aactcacgtt aagggatttt ggtcatgaga ttatcaaaaa ggatcttcac      8460
ctagatcctt ttaaattaaa aatgaagttt taaatcaatc taaagtatat atgagtaaac      8520
ttggtctgac agttaccaat gcttaatcag tgaggcacct atctcagcga tctgtctatt      8580
tcgttcatcc atagttgcct gactccccgt cgtgtagata actacgatac gggagggctt      8640
accatctggc cccagtgctg caatgatacc gcgagaccca cgctcaccgg ctccagattt      8700
atcagcaata aaccagccag ccggaagggc cgagcgcaga agtggtcctg caactttatc      8760
cgcctccatc cagtctatta attgttgccg ggaagctaga gtaagtagtt cgccagttaa      8820 tagtttcgc aacgttgttg ccattgctgc aggtcgggag cacaggatga cgcctaacaa       8880
ttcattcaag ccgacaccgc ttcgcggcgc ggcttaattc aggagttaaa catcatgagg      8940
gaagcggtga tcgccgaagt atcgactcaa ctatcagagg tagttggcgt catcgagcgc      9000
catctcgaac cgacgttgct ggccgtacat ttgtacggct ccgcagtgga tggcggcctg      9060
aagccacaca gtgatattga tttgctggtt acggtgaccg taaggcttga tgaaacaacg      9120
cggcgagctt tgatcaacga ccttttggaa acttcggctt cccctggaga gagcgagatt      9180
ctccgcgctg tagaagtcac cattgttgtg cacgacgaca tcattccgtg gcgttatcca      9240
gctaagcgcg aactgcaatt tggagaatgg cagcgcaatg acattcttgc aggtatcttc      9300
gagccagcca cgatcgacat tgatctggct atcttgctga caaaagcaag agaacatagc      9360
gttgccttgg taggtccagc ggcggaggaa ctctttgatc cggttcctga acaggatcta      9420
tttgaggcgc taaatgaaac cttaacgcta tggaactcgc cgcccgactg ggctggcgat      9480
gagcgaaatg tagtgcttac gttgtcccgc atttggtaca gcgcagtaac cggcaaaatc      9540
gcgccgaagg atgtcgctgc cgactgggca atggagcgcc tgccggccca gtatcagccc      9600
gtcatacttg aagctaggca ggcttatctt ggacaagaag atcgcttggc ctcgcgcgca      9660
gatcagttgg aagaatttgt cactacgtg aaaggcgaga tcaccaaggt agtcggcaaa       9720
taatgtctaa caattcgttc aagccgacgc cgcttcgcgg cgcggcttaa ctcaagcgtt      9780
agatgctgca ggcatcgtgg tgtcacgctc gtcgtttggt atggcttcat tcagctccgg      9840
ttcccaacga tcaaggcgag ttacatgatc ccccatgttg tgcaaaaaag cggttagctc      9900
cttcggtcct ccgatcgagg attttcggc gctgcgctac gtccgcaccg cgttgaggga       9960
```

-continued

```
tcaagccaca gcagcccact cgacctctag ccgacccaga cgagccaagg gatctttttg  10020
gaatgctgct ccgtcgtcag gctttccgac gtttgggtgg ttgaacagaa gtcattatcg  10080
tacggaatgc caagcactcc cgaggggaac cctgtggttg gcatgcacat acaaatggac  10140
gaacggataa acctttcac gcccttttaa atatccgtta ttctaataaa cgctcttttc  10200
tcttaggttt acccgccaat atatcctgtc aaacactgat agtttaaact gaaggcggga  10260
aacgacaatc tgatccccat caagcttgag ctcaggattt agcagcattc cagattgggt  10320
tcaatcaaca aggtacgagc catatcactt tattcaaatt ggtatcgcca aaaccaagaa  10380
ggaactccca tcctcaaagg tttgtaagga agaattctca gtccaaagcc tcaacaaggt  10440
cagggtacag agtctccaaa ccattagcca aaagctacag gagatcaatg aagaatcttc  10500
aatcaaagta aactactgtt ccagcacatg catcatggtc agtaagtttc agaaaaagac  10560
atccaccgaa gacttaaagt tagtgggcat ctttgaaagt aatcttgtca acatcgagca  10620
gctggcttgt ggggaccaga caaaaaagga atggtgcaga attgttaggc gcacctacca  10680
aaagcatctt tgcctttatt gcaaagataa agcagattcc tctagtacaa gtggggaaca  10740
aaataacgtg gaaaagagct gtcctgacag cccactcact aatgcgtatg acgaacgcag  10800
tgacgaccac aaaagaattc cctctatata agaaggcatt cattcccatt tgaaggatca  10860
tcagatactg aaccaatcct tctagaagat ctaagcttat                        10900
```

EXPRESSION OF FRUCTOSE 1,6 BISPHOSPHATE ALDOLASE IN TRANSGENIC PLANTS

This application is a divisional of application Ser. No. 09/098,219 filed Jun. 16, 1998, now U.S. Pat. No. 6,441,277, which is based on U.S. provisional application Serial No. 60/049,955 filed Jun. 17, 1997.

FIELD OF THE INVENTION

This invention relates to the expression of fructose 1,6 bisphosphate aldolase (FDA) in transgenic plants to increase or improve plant growth and development, yield, vigor, stress tolerance, carbon allocation and storage into various storage pools, and distribution of starch. Transgenic plants expressing FDA have increased carbon assimilation, export and storage in plant source and sink organs, which results in growth, yield and quality improvements in crop plants.

BACKGROUND OF THE INVENTION

Recent advances in genetic engineering have provided the prerequisite tools to transform plants to contain alien (often referred to as "heterologous") or improved endogenous genes. These genes can lead either to an improvement of an already existing pathway in plant tissues or to an introduction of a novel pathway to modify product levels, increase metabolic efficiency, and or save on energy cost to the cell. It is presently possible to produce plants with unique physiological and biochemical traits and characteristics of high agronomic and crop processing importance. Traits that play an essential role in plant growth and development, crop yield potential and stability, and crop quality and composition include enhanced carbon assimilation, efficient carbon storage, and increased carbon export and partitioning.

Atmospheric carbon fixation (photosynthesis) by plants represents the major source of energy to support processes in all living organisms. The primary sites of photosynthetic activity, generally referred to as "source organs", are mature leaves and, to a lesser extent, green stems. The major carbon products of source leaves are starch, which represents the transitory storage form of carbohydrate in the chloroplast, and sucrose, which represents the predominant form of carbon transport in higher plants. Other plant parts named "sink organs" (e.g., roots, fruit, flowers, seeds, tubers, and bulbs) are generally not autotrophic and depend on import of sucrose or other major translocatable carbohydrates for their growth and development. The storage sinks deposit the imported metabolites as sucrose and other oligosaccharides, starch and other polysaccharides, proteins, and triglycerides.

In leaves, the primary products of the Calvin Cycle (the biochemical pathway leading to carbon assimilation) are glyceraldehyde 3-phosphate (G3P) and dihydroxyacetone phosphate (DHAP), also known as triose phosphates (triose-P). The condensation of G3P and DHAP into fructose 1,6 bisphosphate (FBP) is catalyzed reversibly by the enzyme fructose 1,6 bisphosphate aldolase (FDA), and various isozymes are known. The acidic isoenzyme appears to be chloroplastic and comprises about 85% of the total leaf aldolase activity. The basic isoenzyme is cytosolic. Both isoenzymes appear to be encoded by the nuclear genome and are encoded by different genes (Lebherz et al., 1984).

In the leaf, the chloroplast FDA is an essential enzyme in the Calvin Cycle, where its activity generates metabolites for starch biosynthesis. Removal of more than 40% of the plastidic aldolase enzymatic activity by antisense technology reduced leaf starch accumulation as well as soluble proteins and chlorophyll levels but also reduced plant growth and root formation (Sonnewald et al., 1994). In contrast, the cytosolic FDA is part of the sucrose biosynthetic pathway where it catalyzes the reaction of FBP production. Moreover, cytosolic FDA is also a key enzyme in the glycolytic and gluconeogenesis pathways in both source and sink plant tissues.

In the potato industry, production of higher starch and uniform solids tubers is highly desirable and valuable. The current potato varieties that are used for french fry production, such as Russet Burbank and Shepody, suffer from a non-uniform deposition of solids between the tuber pith (inner core) and the cortex (outer core). French fry strips that are taken from pith tissue are higher in water content when compared to outer cortex french fry strips; cortex tissue typically displays a solids level of twenty-four percent whereas pith tissue typically displays a solids level of seventeen percent. Consequently, in the french fry production process, the pith strips need to be blanched, dried, and par-fried for longer times to eliminate the excess water. Adequate processing of the pith fries results in the overcooking of fries from the high solids cortex. The blanching, drying, and par frying times of the french fry processor need to be adjusted accordingly to accommodate the low solids pith strips and the high solids cortex strips. A higher solids potato with a more uniform distribution of starch from pith to cortex would allow for a more uniform finished fry product, with higher plant throughput and cost savings due to reduced blanch, dry and par-fry times.

Although various fructose 1,6 bisphosphate aldolases have been previously characterized, it has been discovered that overexpression of the enzyme in a transgenic plant provides advantageous results in the plant such as increasing the assimilation, export and storage of carbon, increasing the production of oils and/or proteins in the plant and improving tuber solids uniformity.

SUMMARY OF THE INVENTION

The present invention provides structural DNA constructs that encode a fructose 1,6 bisphosphate aldolase (FDA) enzyme and that are useful in increasing carbon assimilation, export, and storage in plants.

In accomplishing the foregoing, there is provided, in accordance with one aspect of the present invention, a method of producing genetically transformed plants that have elevated carbon assimilation, storage, export, and improved solids uniformity comprising the steps of:
(a) Inserting into the genome of a plant a recombinant, double-stranded DNA molecule comprising
   (i) a promoter that functions in the cells of a target plant tissue,
   (ii) a structural DNA sequence that causes the production of an RNA sequence that encodes a fructose 1,6 bisphosphate aldolase enzyme,
   (iii) a 3' non-translated DNA sequence that functions in plant cells to cause transcriptional termination and the addition of polyadenylated nucleotides to the 3' end of the RNA sequence;
(b) obtaining transformed plant cells; and
(c) regenerating from transformed plant cells genetically transformed plants that have elevated FDA activity.

In another aspect of the present invention there is provided a recombinant, double-stranded DNA molecule comprising in sequence
   (i) a promoter that functions in the cells of a target plant tissue, (ii) a structural DNA sequence that causes the production of an RNA sequence that encodes a fructose 1,6 bisphosphate aldolase enzyme, (iii) a 3' non-translated DNA sequence that functions in plant cells to cause transcriptional termination and the addition of polyadenylated nucleotides to the 3' end of the RNA sequence.

In a further aspect of the present invention, the structural DNA sequence that causes the production of an RNA sequence that encodes a fructose 1,6 bisphosphate aldolase enzyme is coupled with a chloroplast transit peptide to facilitate transport of the enzyme to the plastid.

In accordance with the present invention, an improved means for increasing carbon assimilation, storage and export in the source tissues of various plants is provided. Further means of improved carbon accumulation in sinks (such as roots, tubers, seeds, stems, and bulbs) are provided, thus increasing the size of various sinks (larger roots, tubers, etc.) and subsequently increasing yield and crop productivity. The increased carbon availability to these sinks would also improve composition and use efficiency in the sink (oil, protein, starch and/or sucrose production, and/or solids uniformity).

Various advantages may be achieved by the aims of the present invention, including:

First, increasing the expression of the FDA enzyme in the chloroplast would increase the flow of carbon through the Calvin Cycle and increase atmospheric carbon assimilation during early photoperiod. This would result in an increase in photosynthetic efficiency and an increase in chloroplast starch production (a leaf carbon storage form degraded during periods when photosynthesis is low or absent). Both of these responses would lead to an increase in sucrose production by the leaf and a net increase in carbon export during a given photoperiod. This increase in source capacity is a desirable trait in crop plants and would lead to increased plant growth, storage ability, yield, vigor, and stress tolerance.

Second, increasing FDA expression in the cytosol of photosynthetic cells would lead to an increase in sucrose production and export out of source leaves. This increase in source capacity is a desirable trait in crop plants and would lead to increased plant growth, storage ability, yield, vigor, and stress tolerance.

Third, expression of FDA in sink tissues can show several desirable traits, such as increased amino acid and/or fatty acid pools via increases in carbon flux through glycolysis (and thus pyruvate levels) in seeds or other sinks and increased starch levels as result of increased production of glucose 6-phosphate in seeds, roots, stems, and tubers where starch is a major storage nonstructural carbohydrate (reverse glycolysis). This increase in sink strength is a desirable trait in crop plants and would lead to increased plant growth, storage ability, yield, vigor, and stress tolerance.

Fourth, the invention is particularly desirable for use in the commercial production of foods derived from potatoes. Potatoes used for the production of french fries and other products suffer from a non-uniform distribution of solids between the tuber pith (inner core) and the cortex (outer core). Thus, french fry strips from the pith regions of such tubers have a low solids content and a high water content in comparison to cortex strips from the same tubers. Therefore, the french fry processor attempts to adjust the processing parameters so that the final inner strips are sufficiently cooked while the outer cortex strips are not overcooked. The results of such adjustments, however, are highly variable and may lead to poor quality product. Transgenic potatoes expressing fda will provide to the french-fry and potato chip processor a raw product that consistently displays a higher tuber solids uniformity with acceptable agronomic traits. In the french fry plant production process, inner pith fry strips from higher solids uniformity tubers will require less time to blanch, less time to dry to a specific solids content, and less time to par-fry before freezing and shipping to retail and institutional end-users.

Therefore, with respect to potatoes, the present invention provides 1) a higher quality, more uniform finish fry product in which french fries from all tuber regions, when processed, are nearly the same, 2) a higher through-put in the french fry processing plant due to lower processing times, and 3) processor cost savings due to lower energy input required for lower blanch, dry, and par-fry times. A raw tuber product that displays a higher solids uniformity will also produce a potato chip that has a reduced saddle curl, and a reduced tendency for center bubble, which are undesirable qualities in the potato chip industry. Reduced fat content would also result; this would contribute to improved consumer appeal and lower oil use (and costs) for the processor. The increase in solids uniformity will also translate to an increase in overall tuber solids. For both the french fry and chipping industries, this overall tuber solids increase will also result in higher through-put in the processing plant due to lower processing times, and cost savings due to lower energy input for blanching, drying, par-frying, and finish frying.

BRIEF DESCRIPTION OF THE DRAWINGS

FIGS. 1a and 1b shows the nucleotide sequence and deduced amino acid sequence of a fructose 1,6 bisphosphate aldolase gene from E. coli (SEQ ID No:1).

DETAILED DESCRIPTION OF THE INVENTION

Figure 2:
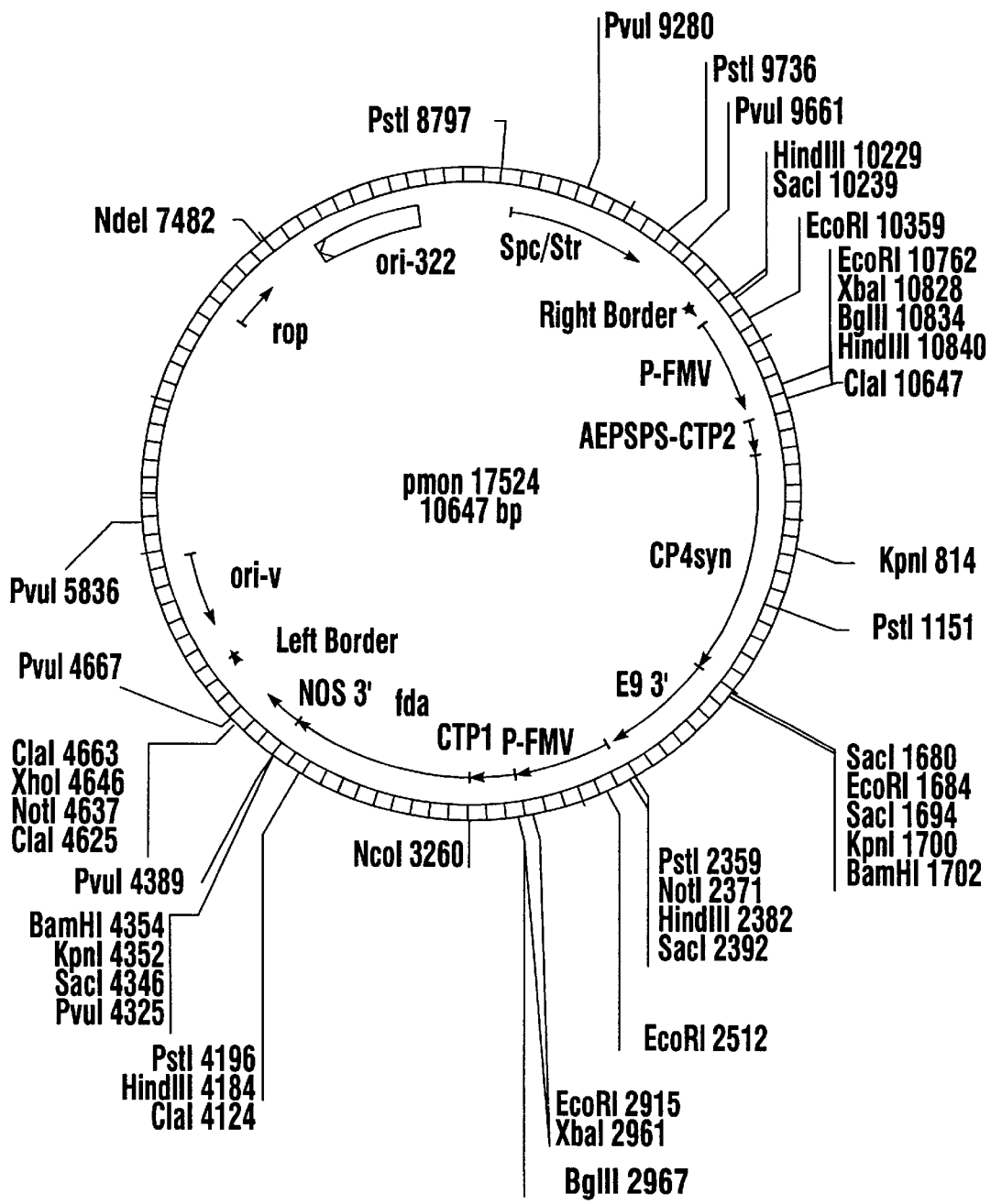
FIG. 2 shows a plasmid map for plant transformation vector pMON17524.

This invention is directed to a method for producing plant cells and plants demonstrating an increased or improved growth and development, yield, quality, starch storage uniformity, vigor, and/or stress tolerance. The method utilizes a DNA sequence encoding an fda (fructose 1,6 bisphosphate aldolase) gene integrated in the cellular genome of a plant as the result of genetic engineering and causes expression of the FDA enzyme in the transgenic plant so produced. Plants that overexpress the FDA enzyme exhibit increased carbon flow through the Calvin Cycle and increased atmospheric carbon assimilation during early photoperiod resulting in an increase in photosynthetic efficiency and an increase in starch production. Thus, such plants exhibit higher levels of sucrose production by the leaf and the ability to achieve a net increase in carbon export during a given photoperiod. This increase in source capacity leads to increased plant growth that in turn generates greater biomass and/or increases the size of the sink and ultimately providing greater yields of the transgenic plant. This greater biomass or increased sink size may be evidenced in different ways or plant parts depending on the particular plant species or growing conditions of the plant overexpressing the FDA enzyme. Thus, increased size resulting from overexpression of FDA may be seen in the seed, fruit, stem, leaf, tuber, bulb or other plant part depending upon the plant species and its dominant sink during a particular growth phase and upon the environmental effects caused by certain growing conditions, e.g. drought, temperature or other stresses. Transgenic plants overexpressing FDA may therefore have increased carbon assimilation, export and storage in plant source and sink organs, which results in growth, yield, and uniformity and quality improvements.

Plants overexpressing FDA may also exhibit desirable quality traits such as increased production of starch, oils and/or proteins depending upon the plant species overexpressing the FDA. Thus, overexpression of FDA in a particular plant species may affect or alter the direction of the carbon flux thereby directing metabolite utilization and storage either to starch production, protein production or oil production via the role of FDA in the glycolysis and gluconeogenesis metabolic pathways.

The mechanism whereby the expression of exogenous FDA modifies carbon relationships is believed to derive from source-sink relationships. The leaf tissue is a sucrose source, and if more sucrose resulting from the activity of increased FDA expression is transported to a sink, it results in increased storage carbon (sugars, starch, oil, protein, etc.) or nitrogen (protein, etc.) per given weight of the sink tissue.

The expression in a plant of a gene that exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region, which adds polyadenylate nucleotides to the 3' end of the RNA. Transcription of DNA into mRNA is regulated by a region of DNA usually referred to as the promoter. The promoter region contains a sequence of bases that signals RNA polymerase to associate with the DNA and to initiate the transcription of mRNA using one of the DNA strands as a template to make a corresponding complimentary strand of RNA. This RNA is then used as a template for the production of the protein encoded therein by the cells protein biosynthetic machinery.

A number of promoters that are active in plant cells have been described in the literature. These include the nopaline synthase (NOS) and octopine synthase (OCS) promoters (which are carried on tumor-inducing plasmids of *Agrobacterium tumefaciens*), the caulimovirus promoters such as the cauliflower mosaic virus (CaMV) 19S and 35S and the figwort mosaic virus (FMV) 35S-promoters, the light-inducible promoter from the small subunit of ribulose-1,5-bisphosphate carboxylase (ssRUBISCO), a very abundant plant polypeptide, and the chlorophyll a/b binding protein gene promoters, etc. All of these promoters have been used to create various types of DNA constructs that have been expressed in plants; see, e.g., PCT publication WO 84/02913.

Promoters that are known to or are found to cause transcription of DNA in plant cells can be used in the present invention. Such promoters may be obtained from a variety of sources such as plants and plant viruses and include, but are not limited to, the enhanced CaMV35S promoter and promoters isolated from plant genes such as ssRUBISCO genes. As described below, it is preferred that the particular promoter selected should be capable of causing sufficient expression to result in the production of an effective amount of fructose 1,6 bisphosphate aldolase enzyme to cause the desired increase in carbon assimilation, export or storage. Expression of the double-stranded DNA molecules of the present invention can be driven by a constitutive promoter, expressing the DNA molecule in all or most of the tissues of the plant. Alternatively, it may be preferred to cause expression of the fda gene in specific tissues of the plant, such as leaf, stem, root, tuber, seed, fruit, etc. The promoter chosen will have the desired tissue and developmental specificity. Those skilled in the art will recognize that the amount of fructose 1,6 bisphosphate aldolase needed to induce the desired increase in carbon assimilation, export, or storage may vary with the type of plant. Therefore, promoter function should be optimized by selecting a promoter with the desired tissue expression capabilities and approximate promoter strength and selecting a transformant that produces the desired fructose 1,6 bisphosphate aldolase activity or the desired change in metabolism of carbohydrates in the target tissues. This selection approach from the pool of transformants is routinely employed in expression of heterologous structural genes in plants because there is variation between transformants containing the same heterologous gene due to the site of gene insertion within the plant genome (commonly referred to as "position effect"). In addition to promoters that are known to cause transcription (constitutively or tissue-specific) of DNA in plant cells, other promoters may be identified for use in the current invention by screening a plant cDNA library for genes that are selectively or preferably expressed in the target tissues of interest and then isolating the promoter regions by methods known in the art. In particular, it may be desirable to use a bundle sheath cell specific (or cell enhanced expression) promoter for use with C4 plants such as corn, sorghum, and sugarcane to obtain the yield benefits of overexpression of FDA and not use a constitutive promoter or a promoter with mesophyll cell enhanced expression properties.

For the purpose of expressing the fda gene in source tissues of the plant, such as the leaf or stem, it is preferred that the promoters utilized in the double-stranded DNA molecules of the present invention have relatively high expression in these specific tissues. For this purpose, one may also choose from a number of promoters for genes with leaf-specific or leaf-enhanced expression. Examples of such genes known from the literature are the chloroplast glutamine synthetase GS2 from pea (Edwards et al., 1990), the chloroplast fructose-1,6-bisphosphatase (FBPase) from wheat (Lloyd et al., 1991), the nuclear photosynthetic ST-LS1 from potato (Stockhaus et al., 1989), and the phenylalanine ammonia-lyase (PAL) and chalcone synthase (CHS) genes from *Arabidopsis thaliana* (Leyva et al., 1995).

Also shown to be active in photosynthetically active tissues are the ribulose-1,5-bisphosphate carboxylase (RUBISCO), isolated from eastern larch (*Larix laricina*) (Campbell et al., 1994); the cab gene, encoding the chlorophyll a/b-binding protein of PSII, isolated from pine (cab6; Yamamoto et al., 1994), wheat (Cab-1; Fejes et al., 1990), spinach (CAB-1; Luebberstedt et al., 1994), and rice (cab1R: Luan et al., 1992); the pyruvate orthophosphate dikinase (PPDK) from maize (Matsuoka et al., 1993); the tobacco Lhcb1*2 gene (Cerdan et al., 1997); the *Arabidopsis thaliana* SUC2 sucrose-H+symporter gene (Truemit et al., 1995); and the thylacoid membrane proteins, isolated from spinach (psaD, psaF, psaE, PC, FNR, atpC, atpD, cab, rbcS; Oelmueller et al., 1992). Other chlorophyll a/b-binding proteins have been studied and described in the literature, such as LhcB and PsbP from white mustard (*Sinapis alba;* Kretsch et al., 1995). Homologous promoters to those described here may also be isolated from and tested in the target or related crop plant by standard molecular biology procedures.

For the purpose of expressing the fda in sink tissues of the plant, for example the tuber of the potato plant; the fruit of tomato; or seed of maize, wheat, rice, or barley, it is preferred that the promoters utilized in the double-stranded DNA molecules of the present invention have relatively high expression in these specific tissues. A number of genes with tuber-specific or tuber-enhanced expression are known, including the class I patatin promoter (Bevan et al., 1986; Jefferson et al., 1990); the potato tuber ADPGPP genes, both the large and small subunits (Muller et al., 1990); sucrose synthase (Salanoubat and Belliard, 1987, 1989); the major tuber proteins including the 22 kDa protein complexes and proteinase inhibitors (Hannapel, 1990); the granule bound starch synthase gene (GBSS) (Rohde et al., 1990); and the other class I and II patatins (Rocha-Sosa et al., 1989; Mignery et al., 1988). Other promoters can also be used to express a fructose 1,6 bisphosphate aldolase gene in specific tissues, such as seeds or fruits. The promoter for β-conglycinin (Tierney, 1987) or other seed-specific promoters, such as the napin and phaseolin promoters, can be used to over-express an fda gene specifically in seeds. The zeins are a group of storage proteins found in maize endosperm. Genomic clones for zein genes have been isolated (Pedersen et al., 1982), and the promoters from these clones, including the 15 kDa, 16 kDa, 19 kDa, 22 kDa, 27 kDa, and gamma genes, could also be used to express an fda gene in the seeds of maize and other plants. Other promoters known to function in maize, wheat, or rice include the promoters for the following genes: waxy, Brittle, Shrunken 2, branching enzymes I and II, starch synthases, debranching enzymes, oleosins, glutelins, and sucrose synthases. Particularly preferred promoters for maize endosperm expression, as well as in wheat and rice, of an fda gene is the promoter for a glutelin gene from rice, more particularly the Osgt-1 promoter (Zheng et al., 1993); the maize granule-bound starch synthase (waxy) gene (zmGBS); the rice small subunit ADPGPP promoter (osAGP);and the zein promoters, particularly the maize 27 kDa zein gene promoter (zm27) (see, generally, Russell et al., 1997). Examples of promoters suitable for expression of an fda gene in wheat include those for the genes for the ADPglucose pyrophosphorylase (ADPGPP) subunits, for the granule bound and other starch synthases, for the branching and debranching enzymes, for the embryogenesis-abundant proteins, for the gliadins, and for the glutenins. Examples of such promoters in rice include those for the genes for the ADPGPP subunits, for the granule bound and other starch synthases, for the branching enzymes, for the debranching enzymes, for sucrose synthases, and for the glutelins. A particularly preferred promoter is the promoter for rice glutelin, Osgt-1. Examples of such promoters for barley include those for the genes for the ADPGPP subunits, for the granule bound and other starch synthases, for the branching enzymes, for the debranching enzymes, for sucrose synthases, for the hordeins, for the embryo globulins, and for the aleurone-specific proteins.

The solids content of root tissue may be increased by expressing an fda gene behind a root-specific promoter. An example of such a promoter is the promoter from the acid chitinase gene (Samac et al., 1990). Expression in root tissue could also be accomplished by utilizing the root-specific subdomains of the CaMV35S promoter that have been identified (Benfey et al., 1989).

The RNA produced by a DNA construct of the present invention may also contain a 5' non-translated leader sequence. This sequence can be derived from the promoter selected to express the gene and can be specifically modified so as to increase translation of the mRNA. The 5' non-translated regions can also be obtained from viral RNAs, from suitable eukaryotic genes, or from a synthetic gene sequence. The present invention is not limited to constructs, as presented in the following examples, wherein the non-translated region is derived from the 5' non-translated sequence that accompanies the promoter sequence. Rather, the non-translated leader sequence can be derived from an unrelated promoter or coding sequence.

In monocots, an intron is preferably included in the gene construct to facilitate or enhance expression of the coding sequence. Examples of suitable introns include the HSP70 intron and the rice actin intron, both of which are known in the art. Another suitable intron is the castor bean catalase intron (Suzuki et al., 1994)

Polyadenylation Signal

The 3' non-translated region of the chimeric plant gene contains a polyadenylation signal that functions in plants to cause the addition of polyadenylate nucleotides to the 3' end of the RNA. Examples of suitable 3' regions are (1) the 3' transcribed, non-translated regions containing the polyadenylation signal of Agrobacterium tumor-inducing (Ti) plasmid genes, such as the nopaline synthase (NOS) gene, and (2) plant genes like the soybean storage protein genes and the small subunit of the ribulose-1,5-bisphosphate carboxylase (ssRUBISCO) gene.

Plastid-Directed Expression of Fructose-1,6-Bisphosphate Aldolase Activity

In one embodiment of the invention, the fda gene may be fused to a chloroplast transit peptide, in order to target the FDA protein to the plastid. As used hereinafter, chloroplast and plastid are intended to include the various forms of plastids including amyloplasts. Many plastid-localized proteins are expressed from nuclear genes as precursors and are targeted to the plastid by a chloroplast transit peptide (CTP), which is removed during the import steps. Examples of such chloroplast proteins include the small subunit of ribulose-1,5-biphosphate carboxylase (ssRUBISCO, SSU), 5-enolpyruvateshikimate-3-phosphate synthase (EPSPS), ferredoxin, ferredoxin oxidoreductase, the light-harvesting-complex protein I and protein II, and thioredoxin F. It has been demonstrated that non-plastid proteins may be targeted to the chloroplast by use of protein fusions with a CTP and that a CTP sequence is sufficient to target a protein to the plastid. Those skilled in the art will also recognize that various other chimeric constructs can be made that utilize the functionality of a particular plastid transit peptide to import the fructose-1,6-diphosphate aldolase enzyme into the plant cell plastid. The fda gene could also be targeted to the plastid by transformation of the gene into the chloroplast genome (Daniell et al., 1998).

Fructose 1,6 Bisphosphate Aldolases

As used herein, the term "fructose 1, 6-bisphophate aldolase" means an enzyme (E.C. 4.1.2.13) that catalyzes the reversible cleavage of fructose 1,6-bisphosphate to form glyceraldehyde 3-phosphate (G3P) and dihydroxyacetone phosphate (DHAP). Aldolase enzymes are divided into two classes, designated class I and class II (Witke and Gotz, 1993). Various fda genes encoding the enzyme have been sequenced, as have numerous proteins, such as the cytosolic enzyme from maize (GenBank Accession S07789;S 10638), cytosolic enzyme from rice (GenBank Accession JQ0543), cytosolic enzyme from spinach (GenBank Accession S31091;S22093), from *Arabidopsis thaliana* (GenBank Accession S11958), from spinach chloroplast (GenBank Accession S31090;A21815;S22092), from yeast (*S. cerevisiae*) (GenBank Accession S07855; S37882; S12945; S39178; S44523;X75781), from *Rhodobacter sphaeroides* (GenBank Accession B40767;D41080), from *B. subtilis* (GenBank Accession S55426; D32354; E32354; D41835), from garden pea (GenBank Accession S29048; S34411), from garden pea chloroplast (GenBank Accession S29047; S34410), from maize (GenBank Accession S05019), from *Chlamydomonas reinhardtii* (GenBank Accession S48639; S58485; S58486; S34367), from *Corynebacterium glutamicum* (GenBank Accession S09283; X17313), from *Campylobacter jejuni* (GenBank Accession S52413), from *Haemophilus influenzae* (strain Rd KW20) (GenBank Accession C64074), from *Streptococcus pneumonia* (GenBank Accession AJ005697), from rice (GenBank Accession X53130), and from the maize anaerobically regulated gene (GenBank Accession X12872).

The class I enzymes may be isolated from higher eukaryotes, such as animals and plants, and in some prokaryotes, including *Peptococcus aerogens*, (Lebherz and Rutter, 1973), *Lactobacillus casei* (London and Kline, 1973), *Escherichia coli* (Stribling and Perham, 1973), *Mycobacterium smegmatis* (Bai et al., 1975), and most staphylococcal species (Gotz et al., 1979). The gene for the FDA enzyme may be obtained by known methods and has already been done so for several organisms, such as rabbit (Lai et al., 1974), human (Besmond et al., 1983), rat (Tsutsumi et al., 1984), *Trypanosoma brucei* (Clayton, 1985), and *Arabidopsis thaliana* (Chopra et al., 1990). These class I enzymes are invariably tetrameric proteins with a total molecular weight of about 160 kDa and function by imine formation between the substrate and a lysine residue in the active site (Alfounder et al., 1989).

In animal, three class I isozymes, classified as A, B, and C, are expressed in the cytosol of muscle, liver, and brain tissue respectively, and they differ from plant aldolases in their expression and compartmentation patterns (Joh et al., 1986). In the leaves of higher plants, FDA is a class I enzyme, and two different isoenzymes within the class have been documented. One is contained in the chloroplast and the other in the cytosol (Lebherz et al., 1984). The acidic plant isozyme appear to be chloroplastic and comprises about 85% of the total leaf aldolase activity. The basic plant isozyme is cytosolic, and both isozymes appear to be encoded by the nuclear genome and are encoded by different genes (Lebherz et al., 1984).

The class II type aldolases are normally dimeric with molecular mass of approximately 80 kDa, and their activity depends on divalent metal ions. The class II enzymes may be isolated from prokaryotes, such as blue-green algae and bacteria, and eukaryotic green algae and fungi (Baldwin et al., 1978). The gene for the FDA class II enzyme may be obtained by known methods and has already been done so from several organisms including *Saccharomyces cerevisiae* (Jack and Harris, 1971), *Bacillus stearothermophilus* (Jack, 1973), and *Escherichia coli* (Baldwin et al., 1978).

It is believed that highly homologous class II fructose 1,6-bisphophate aldolases with similar catalyzing activity will also be found in other species of microorganism, such as Saccharomyces (*Saccharomyces cerevisiae*); Bacillus (*Bacillus subtilis*); Rhodobacter (*Rhodobacter sphaeroides*); Plasmodium (*Plasmodium falciparium, Plasmodium berghei*); Trypanosoma (*Trypanosoma brucei*); Chlamydomonas (*Chlamydomas reinhardtii*); Candida (*Candida albicans*); Corynebacterium (*Corynebacterium glutamicum*); Campylobacter (*Campylobacter jejuni*); and Haemophilus (*Haemophilus influenza*).

Such sequences can be readily isolated by methods well known in the art, for example by nucleic acid hybridization. The hybridization properties of a given pair of nucleic acids are an indication of their similarity or identity. Nucleic acid sequences can be selected on the basis of their ability to hybridize with known fda sequences. Low stringency conditions may be used to select sequences with less homology or identity. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed sequences. Conditions typically employed may include about 0.02 M to about 0.15 M sodium chloride, about 0.5% to about 5% casein, about 0.02% SDS or about 0.1% N-laurylsarcosine, about 0.001 M to about 0.03 M sodium citrate, at hybridization temperatures between about 50° C. and about 70° C. More preferably, high stringency conditions are about 0.02 M sodium chloride, about 0.5% casein, about 0.02% SDS, about 0.001 M sodium citrate, at a temperature of about 50° C. The skilled individual will recognize that numerous variations are possible in the conditions and means by which nucleic acid hybridization can be performed to isolate fda sequences having similarity to fda sequences known in the art and are not limited to those explicitly disclosed herein. Preferably, such an approach is used to isolate fda sequences having greater than about 60% identity with the disclosed *E. coli* fda sequence, more preferably greater than about 70% identity, most preferably greater than about 80% identity.

Depending on growth conditions *Euglena gracilis, Chlamydomonas mundana*, and *Chlamydomomas rheinhardi* produce either a class I or a class II aldolase (Cremona, 1968; Russell and Gibbs, 1967; Guerrini et al., 1971).

The isolation of a class II fda gene from *E. coli* is described in the following examples. Its DNA sequence is given as SEQ ID NO:1 and shown in FIG. 1. The amino acid sequence is shown in SEQ ID NO:2 and shown in FIG. 1. This gene can be used as isolated by inserting it into plant expression vectors suitable for the transformation method of choice as described. The *E. coli* FDA enzyme has an apparent pH optimum range near pH 7–9 and retains activity in the lower pH range of 5–7 (Baldwin et al., 1978; Alfounder et al., 1989).

Thus, many different genes that encode a fructose 1,6 bisphosphate aldolase activity may be isolated and used in the present invention.

Synthetic Gene Construction

A carbohydrate metabolizing enzyme considered in this invention includes any sequence of amino acids, such as protein, polypeptide, or peptide fragment, that demonstrates the ability to catalyze a reaction involved in the synthesis or degradation of starch or sucrose. These can be sequences obtained from a heterologous source, such as algae, bacteria, fungi, and protozoa, or endogenous plant sequences, by which is meant any sequence that can be naturally found in a plant cell, including native (indigenous) plant sequences as well as sequences from plant viruses or plant pathogenic bacteria.

It will be recognized by one of ordinary skill in the art that carbohydrate metabolizing enzyme gene sequences may also be modified using standard techniques such as site-specific mutation or PCR, or modification of the sequence may be accomplished by producing a synthetic nucleic acid sequence and will still be considered a carbohydrate biosynthesis enzyme nucleic acid sequence of this invention. For example, "wobble" positions in codons may be changed such that the nucleic acid sequence encodes the same amino acid sequence, or alternatively, codons can be altered such that conservative amino acid substitutions result. In either case, the peptide or protein maintains the desired enzymatic activity and is thus considered part of this invention.

A nucleic acid sequence to a carbohydrate metabolizing enzyme may be a DNA or RNA sequence, derived from genomic DNA, cDNA, mRNA, or may be synthesized in whole or in part. The structural gene sequences may be cloned, for example, by isolating genomic DNA from an appropriate source and amplifying and cloning the sequence of interest using a polymerase chain reaction (PCR). Alternatively, the gene sequences may be synthesized, either completely or in part, especially where it is desirable to provide plant-preferred sequences. Thus, all or a portion of the desired structural gene may be synthesized using codons preferred by a selected plant host. Plant-preferred codons may be determined, for example, from the codons used most frequently in the proteins expressed in a particular plant host species. Other modifications of the gene sequences may result in mutants having slightly altered activity.

If desired, the gene sequence of the fda gene can be changed without changing the protein sequence in such a manner as may increase expression and thus even more positively affect carbohydrate content in transformed plants. A preferred manner for making the changes in the gene sequence is set out in PCT Publication WO 90/10076. A gene synthesized by following the methodology set out therein may be introduced into plants as described below and result in higher levels of expression of the FDA enzyme. This may be particularly useful in monocots such as maize, rice, wheat, sugarcane, and barley.

Combinations with Other Transgenes

The effect of fda in transgenic plants may be enhanced by combining it with other genes that positively affect carbohydrate assimilation or content, such as a gene encoding for a sucrose phosphorylase as described in PCT Publication WO 96/24679, or ADPGPP genes such as the *E. coli* glgC gene and its mutant glgC16. PCT Publication WO 91/19806 discloses how to incorporate the latter gene into many plant species in order to increase starch or solids. Another gene that can be combined with fda to increase carbon assimilation, export or storage is a gene encoding for sucrose phosphate synthase (SPS). PCT Publication WO 92/16631 discloses one such gene and its use in transgenic plants.

Plant Transformation/Regeneration

In developing the nucleic acid constructs of this invention, the various components of the construct or fragments thereof will normally be inserted into a convenient cloning vector, e.g., a plasmid that is capable of replication in a bacterial host, e.g., *E. coli*. Numerous vectors exist that have been described in the literature, many of which are commercially available. After each cloning, the cloning vector with the desired insert may be isolated and subjected to further manipulation, such as restriction digestion, insertion of new fragments or nucleotides, ligation, deletion, mutation, resection, etc. so as to tailor the components of the desired sequence. Once the construct has been completed, it may then be transferred to an appropriate vector for further manipulation in accordance with the manner of transformation of the host cell.

A recombinant DNA molecule of the invention typically includes a selectable marker so is that transformed cells can be easily identified and selected from non-transformed cells. Examples of such include, but are not limited to, a neomycin phosphotransferase (nptII) gene (Potrykus et al., 1985), which confers kanamycin resistance. Cells expressing the nptII gene can be selected using an appropriate antibiotic such as kanamycin or G418. Other commonly used selectable markers include the bar gene, which confers bialaphos resistance; a mutant EPSP synthase gene (Hinchee et al., 1988), which confers glyphosate resistance; a nitrilase gene, which confers resistance to bromoxynil (Stalker et al., 1988); a mutant acetolactate synthase gene (ALS), which confers imidazolinone or sulphonylurea resistance (European Patent Application 154,204, 1985); and a methotrexate resistant DHFR gene (Thillet et al., 1988).

Plants that can be made to have enhanced carbon assimilation, increased carbon export and partitioning by practice of the present invention include, but are not limited to, Acacia, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassaya, cauliflower, celery, cherry, cilantro, citrus, clementines, coffee, corn, cotton, cucumber, Douglas fir, eggplant, endive, escarole, eucalyptus, fennel, figs, gourd, grape, grapefruit, honey dew, jicama, kiwifruit, lettuce, leeks, lemon, lime, Loblolly pine, mango, melon, mushroom, nut, oat, oil seed rape, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, a vine, watermelon, wheat, yams, and zucchini.

A double-stranded DNA molecule of the present invention containing an fda gene can be inserted into the genome of a plant by any suitable method. Suitable plant transformation vectors include those derived from a Ti plasmid of *Agrobacterium tumefaciens*, as well as those disclosed, e.g., by Herrera-Estrella et al. (1983), Bevan (1984), Klee et al. (1985) and EPO publication 120,516. In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen. DNA may also be inserted into the chloroplast genome (Daniell et al., 1998).

A plasmid expression vector suitable for the introduction of an fda gene in monocots using microprojectile bombardment is composed of the following: a promoter that is specific or enhanced for expression in the starch storage tissues in monocots, generally the endosperm, such as promoters for the zein genes found in the maize endosperm (Pedersen et al., 1982); an intron that provides a splice site to facilitate expression of the gene, such as the Hsp70 intron (PCT Publication WO93/19189); and a 3' polyadenylation sequence such as the nopaline synthase 3' sequence (NOS 3'; Fraley et al., 1983). This expression cassette may be assembled on high copy replicons suitable for the production of large quantities of DNA. A particularly useful Agrobacterium-based plant transformation vector for use in transformation of dicotyledonous plants is plasmid vector pMON530 (Rogers et al., 1987). Plasmid pMON530 is a derivative of pMON505 prepared by transferring the 2.3 kb StuI-HindIII fragment of pMON316 (Rogers et al., 1987) into pMON526. Plasmid pMON526 is a simple derivative of pMON505 in which the SmaI site is removed by digestion with XmaI, treatment with Klenow polymerase and ligation. Plasmid pMON530 retains all the properties of pMON505 and the CaMV35S-NOS expression cassette and now contains a unique cleavage site for SmaI between the promoter and polyadenylation signal.

Binary vector pMON505 is a derivative of pMON200 (Rogers et al., 1987) in which the Ti plasmid homology region, LIH, has been replaced with a 3.8 kb HindIII to SmaI segment of the mini RK2 plasmid, pTJS75 (Schmidhauser and Helinski, 1985). This segment contains the RK2 origin of replication, oriV, and the origin of transfer, oriT, for conjugation into Agrobacterium using the tri-parental mating procedure (Horsch and Klee, 1986). Plasmid pMON505 retains all the important features of pMON200 including the synthetic multi-linker for insertion of desired DNA fragments, the chimeric NOS/NPTII'/NOS gene for kanamycin resistance in plant cells, the spectinomycin/streptomycin resistance determinant for selection in *E. coli* and *A. tumefaciens*, an intact nopaline synthase gene for facile scoring of transformants and inheritance in progeny, and a pBR322 origin of replication for ease in making large amounts of the vector in *E. coli*. Plasmid pMON505 contains a single T-DNA border derived from the right end of the pTiT37 nopaline-type T-DNA. Southern blot analyses have shown that plasmid pMON505 and any DNA that it carries are integrated into the plant genome, that is, the entire plasmid is the T-DNA that is inserted into the plant genome. One end of the integrated DNA is located between the right border sequence and the nopaline synthase gene and the other end is between the border sequence and the pBR322 sequences.

Another particularly useful Ti plasmid cassette vector is pMON17227. This vector is described in PCT Publication WO 92/04449 and contains a gene encoding an enzyme conferring glyphosate resistance (denominated CP4), which is an excellent selection marker gene for many plants, including potato and tomato. The gene is fused to the Arabidopsis EPSPS chloroplast transit peptide (CTP2) and expressed from the FMV promoter as described therein.

When adequate numbers of cells (or protoplasts) containing the fda gene or cDNA are obtained, the cells (or protoplasts) are regenerated into whole plants. Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, canola/rapeseed, etc.), Cucurbitaceae (melons and cucumber), Gramineae (wheat, barley, rice, maize, etc.), Solanaceae (potato, tobacco, tomato, peppers), various floral crops, such as sunflower, and nut-bearing trees, such as almonds, cashews, walnuts, and pecans. See, e.g., Ammirato et al. (1984); Shimamoto et al. (1989); Fromm (1990); Vasil et al. (1990); Vasil et al. (1992); Hayashimoto (1990); and Datta et al. (1990).

The following definitions are provided in order to aid those skilled in the art in understanding the detailed description of the present invention.

The term "promoter" or "promoter region" refers to a nucleic acid sequence, usually found upstream (5') to a coding sequence, that controls expression of the coding sequence by controlling production of messenger RNA (mRNA) by providing the recognition site for RNA polymerase or other factors necessary for start of transcription at the correct site. As contemplated herein, a promoter or promoter region includes variations of promoters derived by means of ligation to various regulatory sequences, random or controlled mutagenesis, and addition or duplication of enhancer sequences. The promoter region disclosed herein, and biologically functional equivalents thereof, are responsible for driving the transcription of coding sequences under their control when introduced into a host as part of a suitable recombinant vector, as demonstrated by its ability to produce mRNA.

"Regeneration" refers to the process of growing a plant from a plant cell (e.g., plant protoplast or explant).

"Transformation" refers to a process of introducing an exogenous nucleic acid sequence (e.g., a vector, recombinant nucleic acid molecule) into a cell or protoplast in which that exogenous nucleic acid is incorporated into a chromosome or is capable of autonomous replication.

A "transformed cell" is a cell whose DNA has been altered by the introduction of an exogenous nucleic acid molecule into that cell.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression.

"Identity" refers to the degree of similarity between two nucleic acid or protein sequences. An alignment of the two sequences is performed by a suitable computer program. A widely used and accepted computer program for performing sequence alignments is CLUSTALW v1.6 (Thompson et al., 1994). The number of matching bases or amino acids is divided by the total number of bases or amino acids and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between 200 and a 400 amino acid proteins, they are 50 percent identical with respect to the shorter sequence. If the shorter sequence is less than 50 bases or amino acids in length, the number of matches are divided by 50 and multiplied by 100 to obtain a percent identity.

"C-terminal region" refers to the region of a peptide, polypeptide, or protein chain from the middle thereof to the end that carries the amino acid having a free carboxyl group.

The phrase "DNA segment heterologous to the promoter region" means that the coding DNA segment does not exist in nature in the same gene with the promoter to which it is now attached.

The term "encoding DNA" refers to chromosomal DNA, plasmid DNA, cDNA, or synthetic DNA that encodes any of the enzymes discussed herein.

The term "genome" as it applies to bacteria encompasses both the chromosome and plasmids within a bacterial host cell. Encoding DNAs of the present invention introduced into bacterial host cells can therefore be either chromosomally integrated or plasmid-localized. The term "genome" as it applies to plant cells encompasses not only chromosomal DNA found within the nucleus, but organelle DNA found within subcellular components of the cell. DNAs of the present invention introduced into plant cells can therefore be either chromosomally integrated or organelle-localized.

The terms "microbe" or "microorganism" refer to algae, bacteria, fungi, and protozoa.

The term "mutein" refers to a mutant form of a peptide, polypeptide, or protein.

"N-terminal region" refers to the region of a peptide, polypeptide, or protein chain from the amino acid having a free amino group to the middle of the chain.

"Overexpression" refers to the expression of a polypeptide or protein encoded by a DNA introduced into a host cell, wherein said polypeptide or protein is either not normally present in the host cell, or wherein said polypeptide or protein is present in said host cell at a higher level than that normally expressed from the endogenous gene encoding said polypeptide or protein.

The term "plastid" refers to the class of plant cell organelles that includes amyloplasts, chloroplasts, chromoplasts, elaioplasts, eoplasts, etioplasts, leucoplasts, and proplastids. These organelles are self-replicating and contain what is commonly referred to as the "chloroplast genome," a circular DNA molecule that ranges in size from about 120 kb to about 217 kb, depending upon the plant species, and which usually contains an inverted repeat region.

The phrase "simple carbohydrate substrate" means a monosaccharide or an oligosaccharide but not a polysaccharide; simple carbohydrate substrate includes glucose, fructose, sucrose, lactose. More complex carbohydrate substrates commonly used in media such as corn syrup, starch, and molasses can be broken down to simple carbohydrate substrates.

The term "solids" refers to the nonaqueous component of a tuber (such as in potato) or a fruit (such as in tomato) comprised mostly of starch and other polysaccharides, simple carbohydrates, nonstructural carbohydrated, amino acids, and other organic molecules.

The following examples are provided to better elucidate the practice of the present invention and should not be interpreted in any way to limit the scope of the present invention. Those skilled in the art will recognize that various modifications, truncations, etc., can be made to the methods and genes described herein while not departing from the spirit and scope of the present invention.

EXAMPLES

Example 1
cDNA Cloning and Overexpression

Unless otherwise stated, basic DNA manipulations and genetic techniques, such as PCR, agarose electrophoresis, restriction digests, ligations, E. coli transformations, colony screens, and Western blots were performed essentially by the protocols described in Sambrook et al. (1989) or Maniatis et al. (1982).

The E. coli fda gene sequence (SEQ ID NO: 1) was obtained from Genbank (Accession Number X14682) and nucleotide primers with homology to the 5' and 3' end were designed for PCR amplification. E. coli chromosomal DNA was extracted and the E. coli fda gene was amplified by PCR using the 5' oligonucleotide 5'GGGGCCATGGCTAAGATTTTTGATTTCGTA3' (SEQ ID NO:3) and the 3' oligonucleotide 5'CCCCGAGCTCTTACAGAACGTCGATCGCGTTCAG3' (SEQ ID NO:4). The PCR cycling conditions were as follows: 94° C., 5 min (1 cycle); addition of polymerase; 94° C., 1 min., 60° C., 1 min., 72° C., 2 min. 30 sec. (35 cycles). The 1.08 kb PCR product was gel purified and ligated into an E. coli expression vector, pMON5723, to form a vector construct that was used for transformation of frozen competent E. coli JM101 cells. The pMON5723 vector contains the E. coli recA promoter and the T7 gene 10 leader (G10L) sequences, which enable high level expression in E. coli (Wong et al., 1988). After induction of the transformed cells, a distinct protein band of about 40 kDa was apparent on an SDS PAGE gel, which correlates with the size of the subunit polypeptide chain of the dimeric aldolase II. It was shown that most of the induced protein was present in the soluble phase. A gel slice containing the highly induced protein was isolated and antibodies were produced in a goat, which was injected with the homogenized gel slice (emulsified in Freund's complete adjuvant).

The fda gene sequence was subsequently cloned into another E. coli expression vector, under the control of the taq promoter. Induction with IPTG of JM101 cells transformed with this vector showed the same 40 kDa overexpressed protein band. This new clone was used in an enzyme assay for FDA activity. Cells transformed with this vector construct were grown in a liquid culture, induced with IPTG, and grown for another 3 hours. Subsequently, a 3 mL cell culture was spun down, dissolved in 100 mM Tris and sonicated. The cell pellet was spun down, and the crude cell extract supernatant was assayed for FDA activity, using a coupled enzymatic assay as described by Baldwin et al. (1978). This assay was routinely performed at 30° C.

The reaction was performed in a 1 mL final volume in excess presence of the enzymes triosephosphate isomerase (TIM) and alpha-glycerophosphate dehydrogenase (GDH) in a reaction mixture containing final concentrations of 100 mM Tris pH 8.0, 4.75 mM fructose 1,6 bisphosphate, 0.15 mM NADH, 500 U/mL TIM, and 30 U/mL GDH.

The decrease in absorbance at 340 nm, after addition of the cell extract supernatant, was recorded using an HP diode array spectrophotometer. One international unit (I.U.) of aldolase activity is that causing the oxidation of 2 $\mu$mol of NAD/min in this assay system.

Cell extracts containing the vector with the fda sequence showed a substantial increase in aldolase activity (13.1 I.U./mg protein) as compared to cells transformed with the control vector (0.15 I.U./mg protein). The activity was shown to be inhibited by EDTA, known to specifically inhibit class II aldolases.

Example 2
Plant Transformation and fda Expression in Tobacco
Targeting of FDA Protein E. coli fructose 1,6 bisphosphate aldolase was targeted to the plastid in plants in order to assess its influence on carbohydrate metabolism and starch biosynthesis in these plant organelles. To accomplish the import of the E coli aldolase into the plastids, a vector was constructed in which the aldolase was fused to the Arabidopsis small subunit transit peptide (CTP1) (Stark et al., 1992) or the maize small subunit CTP (Russell et al., 1993), creating constructs in which the CTP-fda fusion gene was located between the 35S promoter from the figwort mosaic virus (P-FMV35S; Gowda et al., 1989) and the 3'-nontranslated region of the nopaline synthase gene (NOS 3'; Fraley et al., 1983) sequences. The vector construct containing the expression cassette [P-FMV/CTP1/fda/NOS3'] was subsequently used for tobacco protoplast transformation, which was performed as described in Fromm et al. (1987), with the following modifications. Tobacco cultivar Xanthi line D (Txd) cell suspensions were grown in 250-mL flasks, at 25° C. and 138 rpm in the dark. For maintenance, a sub-culture volume of 9 mL was removed and added to 40 mL of fresh Txd media containing MS salts, 3% sucrose, 0.2 g/L inositol, 0.13 g/L asparagine, 80 µL of a 50 mg/mL stock of PCPA, 5 µL of a 1 mg/mL stock of kinetin, and 1 mL of 1000× vitamins (1.3 g/L nicotinic acid, 0.25 g/L thiamine, 0.25 g/L pyridoxine HCL, and 0.25 g/L calcium pantothenate) every 3 to 4 days. Protoplasts were isolated from 1-day-old suspension cells that came from a 2-day-old culture. Sixteen milliliters of cells were added to 40 mL of fresh Txd media and allowed to grow 24 hours prior to digestion and isolation of the protoplasts. The centrifugation stage for the enzyme mix has been eliminated. The electroporation buffer and protoplast isolation media were filter sterilized rather than autoclaved. The electroporation buffer did not have 4 mM $CaCl_2$ added. The suspension cells were digested in enzyme for 1 hour. Protoplasts were counted on a hemacytometer, counting only the protoplasts that look intact and circular. Bio-rad Gene Pulser cuvettes (catalog # 165–2088) with a 0.4-cm gap and a maximum volume of 0.8 mL were used for the electroporations. Fifty to 100 µg of DNA containing the gene of interest along with 5 µg of internal control DNA containing the luciferase gene were added per cuvette. The final protoplast density at electroporation was $2\times10^6$/mL and electroporater settings were a 500 µFarad capacitance and 140 volts on the Bio-rad Gene Pulser. Protoplasts were put on ice after resuspension in electroporation buffer and remained on ice in cuvettes until 10 minutes after electroporation. Protoplasts were added to 7 mL of Txd media+0.4 M mannitol and conditioning media after electroporation. At this stage coconut water was no longer used. The protoplasts were grown in 1-hour day/night photoperiod regime at 26° C. and were spun down and assayed or frozen 20–24 hours after electroporation.

Western blot analysis performed on the protoplast extracts, obtained after transformation, showed processing into the mature FDA in the tobacco protoplasts. Expression was detected of a protein migrating at approximately 40 kDa, which is the molecular weight of the aldolase subunit and the size of the protein also observed after overexpression of the aldolase in *E coli*.

The expression cassette [P-FMV/CTP1/fda/NOS3'] was subsequently cloned into the NotI site of pMON17227 (described in PCT Publication WO 92/04449), in the same orientation as the selectable marker expression cassette, to form the plant transformation vector pMON17524, as shown in FIG. 2 (SEQ ID NO: 5).

An additional construct was made and used for tobacco protoplast transformation, fusing the fda gene to the Arabidopsis EPSPS transit peptide (CTP2), which is described in U.S. Pat. No. 5,463,175. The transit peptide was cloned (through the SphI site) into the SphI site located immediately upstream from the N-terminus of the fda gene sequence in the CTP1-fda fusion (described above). This new CTP2-fda fusion gene was then cloned into a vector between the FMV promoter and the NOS 3' sequences. When this construct containing the CTP2/fda gene sequences was used for tobacco protoplast transformation, expression was detected of a protein migrating at approximately 40 kDa, which is the molecular weight of the aldolase subunit and the size of the protein also observed after overexpression of the aldolase in *E. coli*.

Figure 3:
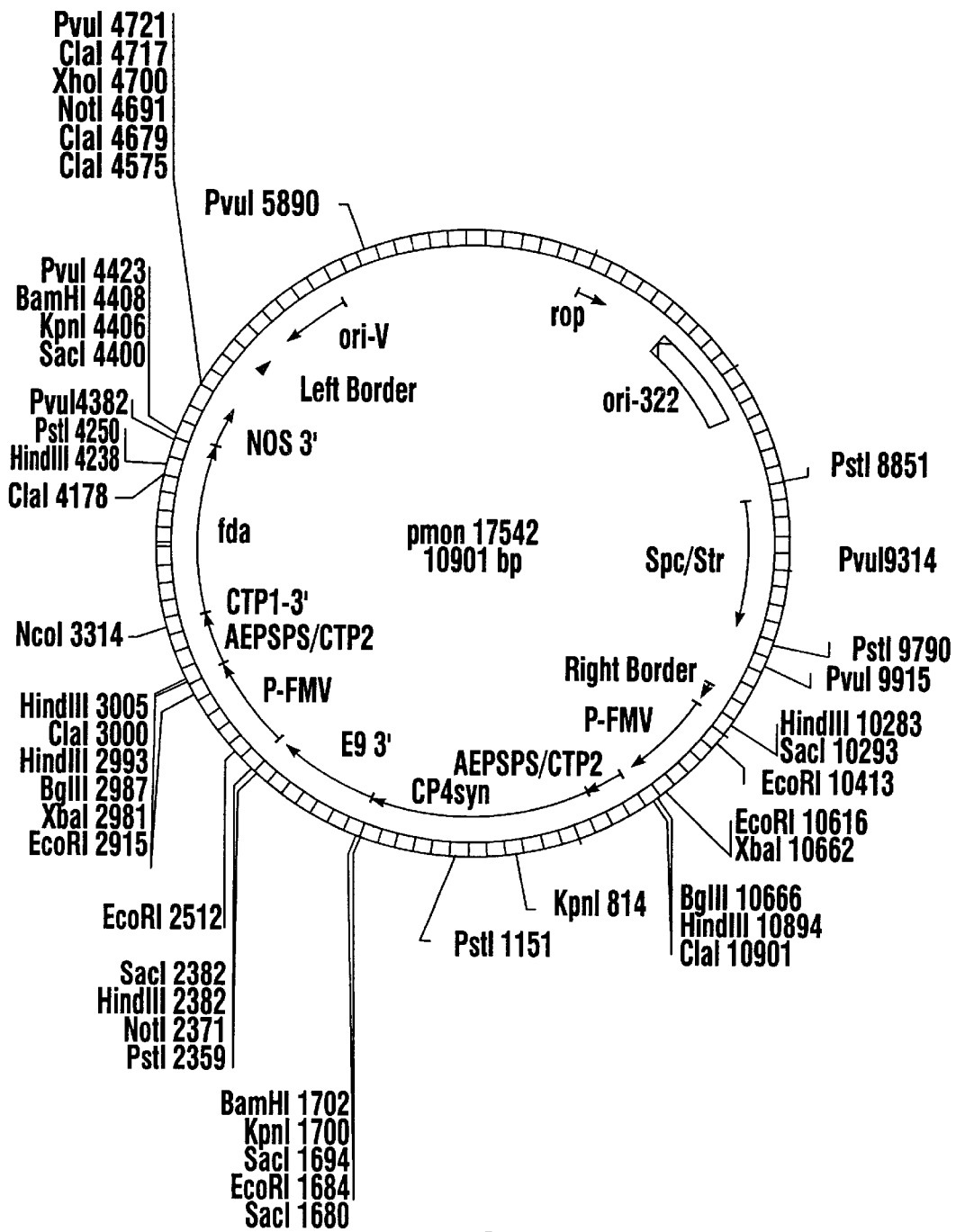
FIG. 3 shows a plasmid map for plant transformation vector pMON17542.

The NotI cassette [P-FMV/CTP2/fda/NOS3'] from this construct was then cloned into the NotI site of pMON17227, in the same orientation as the selectable marker expression cassette, to form the plant transformation vector pMON17542, which is shown in FIG. 3 (SEQ ID NO:6).

For cytoplasmic expression of the FDA in tobacco protoplasts, a construct was made in which the fda gene sequence (without being coupled to a transit peptide) was cloned into a vector backbone, between the FMV promoter and the NOS 3' sequences. Using this construct for tobacco protoplast transformation also showed expression of a protein of the same size, migrating at approximately 40 kDa.

fda Expression in Tobacco Plants

Two constructs, containing the fda gene, fused to the Arabidopsis small subunit CTP1 (pMON17524) (SEQ ID NO:5, FIG. 2) and the Arabidopsis EPSPS (CTP2) transit peptide (pMON17542) (SEQ ID NO:6, FIG. 3), were used for tobacco plant transformation, as described in U.S. Pat. No. 5,463,175. A vector without the CTP-fda sequences, pMON17227 (described in PCT Publication WO 92/04449), was used as a negative control. The plant transformation vectors were mobilized into the ABI Agrobacterium strain. Mating of the plant vector into the ABI strain was done by the triparental conjugation system using the helper plasmid pRK2013 (Ditta et al., 1980).

Growth chamber-grown tobacco transformant lines were generated and first screened by Western blot analysis to identify expressors using goat antibody raised against *E. coli*-expressed fda. Subsequently, for pMON17524-expressing tobacco lines, leaf nonstructural carbohydrates were analyzed (sucrose, glucose, and hydrolyzed starch into glucose) by means of a YSI Instrument, Model 2700 Select Biochemistry Analyzer. Starting at flowering stage, leaf samples were also taken from these plants and analyzed for diurnal changes in leaf nonstructural carbohydrates.

Five hundred milligrams to 1 g fresh tobacco leaf tissue samples were harvested and extracted in 5 mL of hot Na-phosphate buffer (40 g/L $NaH_2PO_4$ and 10 g/L $Na_2H_2PO_4$ in double de-ionized water) by homogenization with a Polytron. Test tubes were then placed in an 85° C. water bath for 15 minutes. Tubes were centrifuged for 12 minutes at 3000 rpm and the supernatants saved for soluble sugar analysis. The pellet was resuspended in 5 mL of hot Na-phosphate buffer mixed with a Vortex and centrifuged as described above. The supernatant was carefully removed and added to the previous supernatant fraction for soluble sugar (sucrose and glucose) analysis by YSI using appropriate membranes.

The starch was extracted from the pellet using the Megazyme Kit (Megazyme, Australia). To the pellet, 200 µL of 50% ethanol and 3 mL of thermostable alpha-amylase (300U) were added and the mixture vortexed. Samples were then incubated in boiling water for 6 minutes and stirred after 2 and 4 minutes. Tubes were placed in 50° C. water bath and 4 mL of 200 mM acetate buffer (pH 4.5) were added followed by 0.1 mL amyloglucosidase (20 U). Incubation occurred for 1 hour. Test tubes were then centrifuged for 15 minutes at 3000 rpm. Aliquots were taken from the supernatant and analyzed for glucose by YSI. The free glucose was adjusted to anhydrous glucose (as it occurs in starch by multiplying by the ratio 162/182). The total volume per tube was 7.1 mL.

Figure 4A:
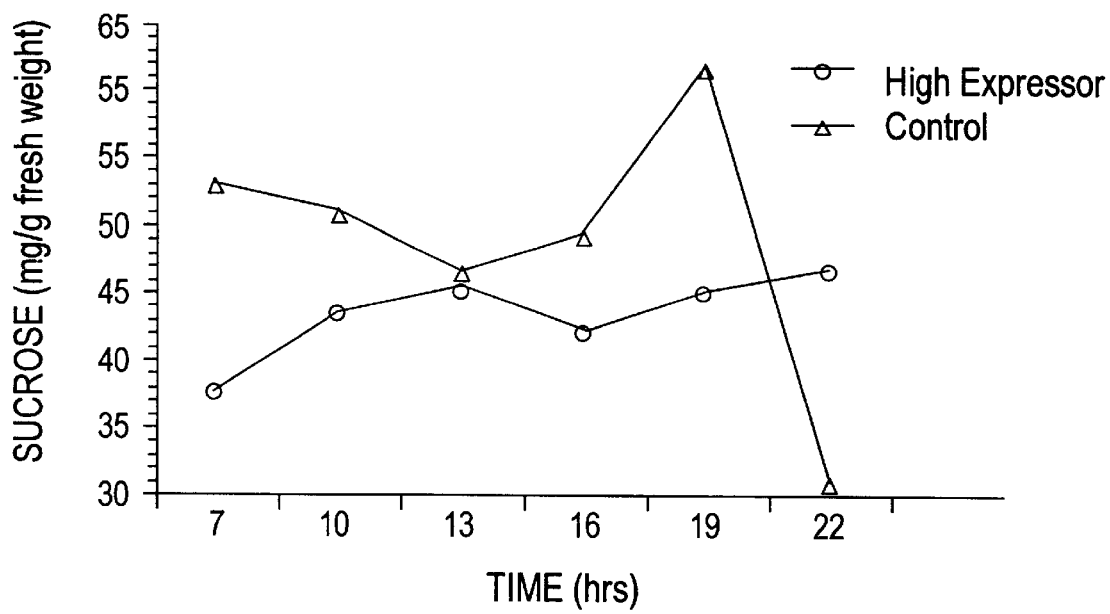
FIG. 4A shows the change in diurnal fluctuation of sucrose levels in tobacco leaves expressing the fda transgene (pMON17524) and control (pMON17227). The light period is from 7:00 to 19:00 hours. Only fully expanded and non-senescing leaves were sampled.
Figure 4B:
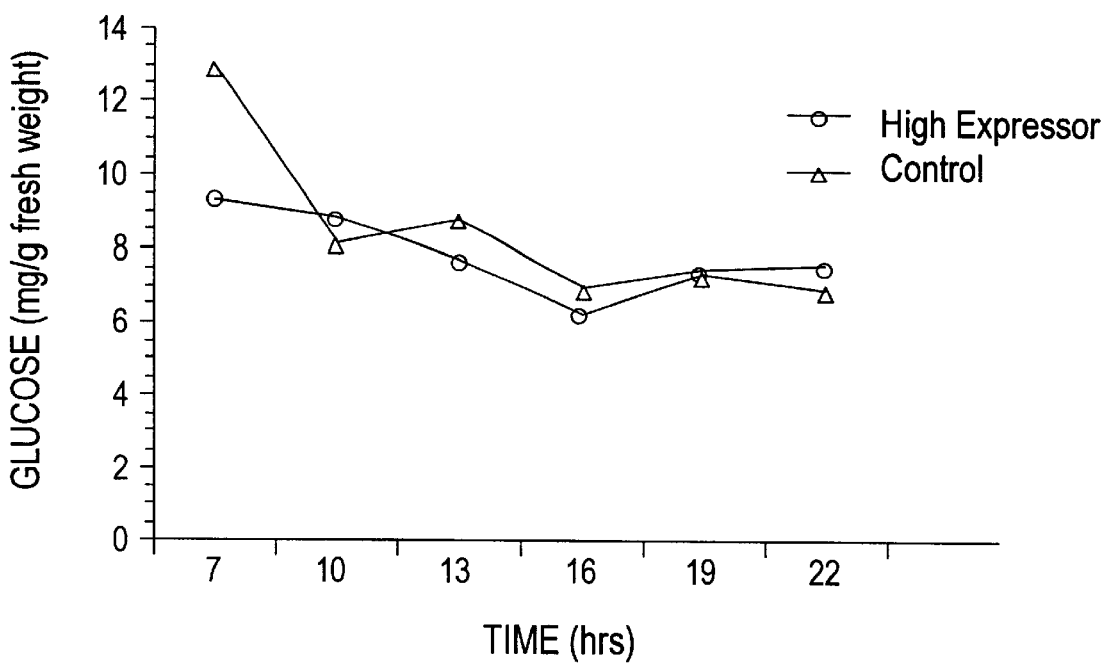
FIG. 4B shows the change in diurnal fluctuation of glucose levels in tobacco leaves expressing the fda transgene (pMON17524) and control (pMON17227). The light period is from 7:00 to 19:00 hours. Only fully expanded and non-senescing leaves were sampled.
Figure 4C:
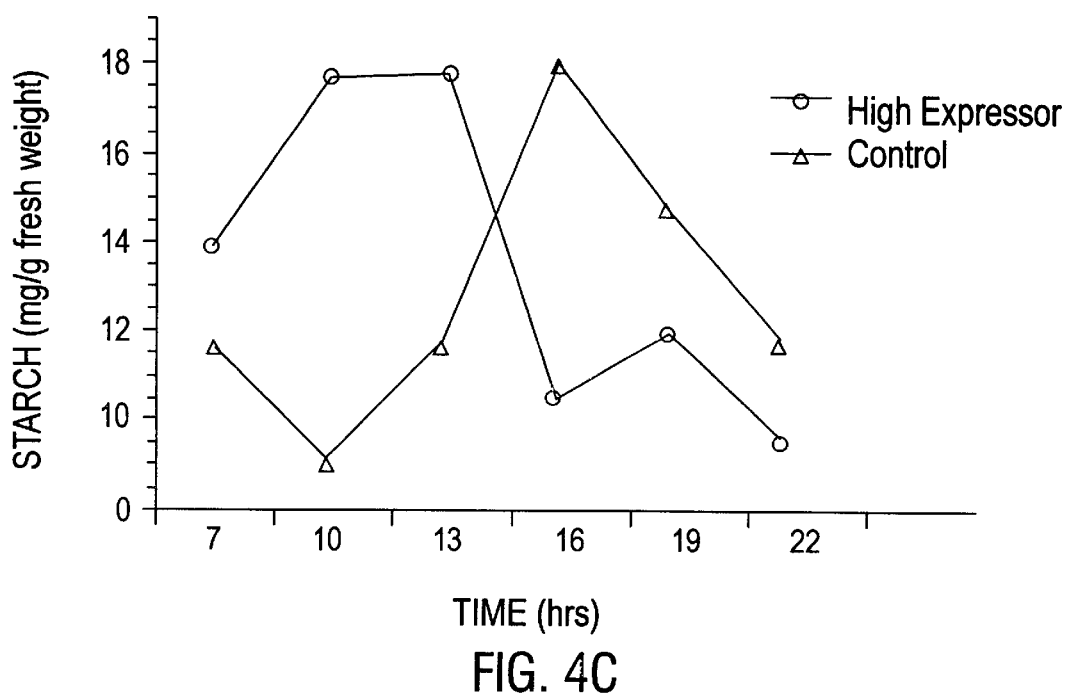
FIG. 4C shows the change in diurnal fluctuation of starch levels in tobacco leaves expressing the fda transgene (pMON17524) and control (pMON17227). The light period is from 7:00 to 19:00 hours. Only fully expanded and non-senescing leaves were sampled.

As seen in Table 1, expression of the fda gene in tobacco correlated with a significant increase in leaf starch levels. However, referring to FIG. 4, when a diurnal profile of starch levels was established in the fda-expressing leaves, this increase was apparent mainly early in the photoperiod, which is a phase when leaves are known to have peak photosynthetic activity. This increase in starch has no apparent negative effect on the plant because the increased starch is turned over during the dark period. There was no apparent increase in steady state levels of sucrose or glucose in tobacco leaves expressing E. coli fda as compared to the control.

TABLE 1

Leaf Carbohydrate Levels of Plants Expressing the fda Transgene[1] (pMON17524)

|  | High Expressors (>0.01% total protein) | Low Expressors (<0.01%) (mg/g fresh weight) | Negative Control |
|---|---|---|---|
| STARCH | 35.08 ± 2.84 | 23.25 ± 3.20 | 16.69 ± 2.92 |
| SUCROSE | 0.97 ± 0.17 | 0.86 ± 0.25 | 0.66 ± 0.19 |
| GLUCOSE | 1.88 ± 0.17 | 1.58 ± 0.20 | 1.68 ± 0.26 |

[1]Leaf samples were harvested at midday.

A second set of transgenic tobacco plants transformed with the construct pMON17542 were grown in the greenhouse. Tobacco plants containing a vector without the CTP-fda sequences, pMON17227, were used as negative control. Of all the pMON17542-lines screened for expression by Western blot analysis, 18 were high expressors (>0.01% of the total cellular protein) and 15 lines were low expressors (<0.01%). Fifteen plants containing the null vector, pMON17227, were used as control. Fully expanded leaves from plants expressing the fda transgene and negative controls were tested for sucrose export by collecting phloem exudate from excised leaf systems. The phloem exudation technique is described in Groussol et al. (1986). Leaves were harvested at 11:30 AM and placed in an exudation medium, containing 5 mM EDTA at pH 6.0, and allowed to exude for a period of 4 hours under full light and high humidity. The exudation solution was immediately analyzed for sucrose level, as described above in the carbohydrate analysis method. As seen in Table 2, a significant increase in sucrose export out of source leaves was observed in plants expressing the fda transgene.

This increase in sucrose export by fda-expressing leaves is an illustration of an increase in source capacity, very likely due to an increased carbon flow through the Calvin Cycle (in response to increased triose-P utilization) and thus an increase in net carbon utilization by the leaf. As seen in Table 2, the increase in sucrose loading in the phloem correlates with the level of fda expression.

TABLE 2

Levels of Sucrose in Phloem Exudate from Excised Leaves of fda Transgenic Tobacco Plants (pMON17542)

|  | Water uptake | sucrose in phloem exudate | |
|---|---|---|---|
|  | (μl/g F.Wt./h) | (ng/leaf) | (ng/g F.Wt.) |
| fda high expressors | 320 ± 20 | 330 ± 60 | 108 ± 22 |
| fda low expressors | 340 ± 10 | 210 ± 10 | 77 ± 3 |
| Control | 390 ± 30 | 160 ± 10 | 56 ± 3 |

Referring to Table 3, preliminary analysis of plant growth and development revealed no significant differences in number of leaves or pods per plant, plant height, stem diameter, or apparent seed weight per plant, between plants expressing the fda gene and the vector control under the specific growing and analysis conditions. However, as seen in Table 4, the fda-transgenic plants had a significantly higher root mass. This may be an indication that, under these conditions, roots represented a more dominant sink that attracted excess carbohydrate produced by the source leaves. Furthermore, the present illustration shows that the increase in root mass in the presence of the E. coli fda gene was accomplished with no apparent negative effect on shoot growth, inflorescence, or seed set. Therefore, this increase in root growth and final root dry weight is a desirable plant trait because it would lead to a rapid seedling establishment following germination and greater plant ability to tolerate drought, cold stress, other environmental challenges, and transplanting. In different plants and under different growing conditions, other plant parts (such as seed, fruit, stem, leaf, tuber, bulb, etc.) are expected to show the weight increase observed in tobacco roots overexpressing the fda transgene.

TABLE 3

Assessment of Certain Plant Growth and Development Parameters in Tobacco Expressing the fda Transgene[1] (pMON17542)

|  | #pods/plant | #leaves/plant | Plant height (cm) | Seed weight (g/plant) |
|---|---|---|---|---|
| high expressors | 162 ± 40 | 25.4 ± 0.8 | 65.3 ± 3.1 | 18.8 ± 2.4 |
| Control | 156 ± 28 | 24.4 ± 0.5 | 65.8 ± 5.1 | 17.3 ± 2.6 |

[1]To achieve this analysis, 14 high-expressor lines were compared to 15 control plants. Measurements were made prior to seed harvest (most pods have reached maturity). The number of leaves was confirmed by counting the number of nodes to account for leaf drop.

TABLE 4

Tobacco Root Dry Weight of Plants Expressing the E.coli fda Transgene[1] (pMON17542)

|  | Root Dry Weight (g/plant) |
|---|---|
| fda high expressors | 64.0 ± 3.9 |
| fda low expressors | 62.7 ± 5.4 |
| Control | 31.7 ± 1.6 |

[1]Roots from 5 high and 7 low expressing lines and 6 control plants were excised and washed carefully then placed in a 65° C. drying oven for at least 48 hours. Roots were removed from the oven and allowed to equilibrate in the laboratory for 2 hours before dry weight determination.

Example 3
Plant Transformation and fda Expression in Corn Plants
Targeting of FDA Protein Vectors containing the fda gene with and without the plastid targeting peptide were made for transformation in corn and are also suitable for other monocots, including rice, wheat, barley, sugarcane, triticale, etc.

Figure 5:
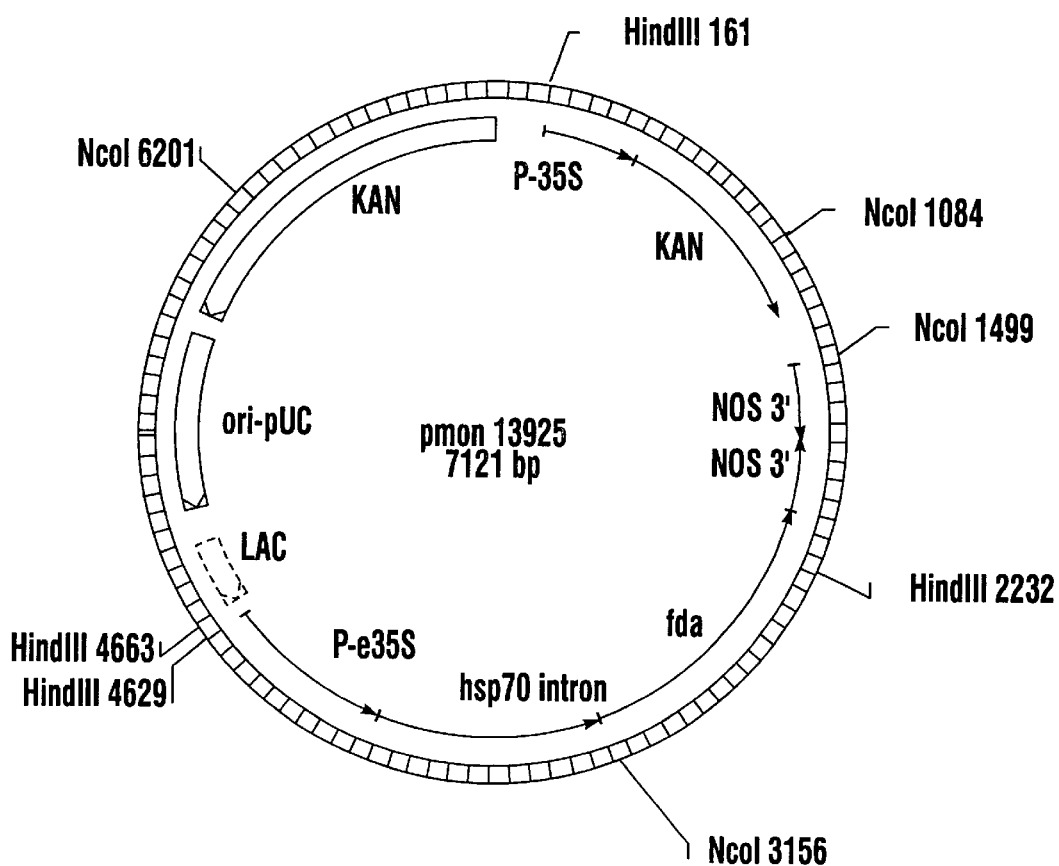
FIG. 5 shows a plasmid map for plant transformation vector pMON13925.

For the cytosolic expression of the fda gene in corn plants, a construct was made in which the fda gene sequence was fused to the backbone of a vector containing the enhanced CaMV 35S promoter (e35S; Kay et al., 1987), the HSP70 intron (U.S. Pat. No. 5,593,874), and the NOS3' polyadenylation sequence (Fraley et al., 1983). This created a NotI cassette [P-e35S/HSP70 intron/fda/NOS3'] that was cloned into the NotI site of pMON30460, a monocot transformation vector, to form the plant transformation vector pMON13925, as shown in FIG. 5. pMON30460 contains an expression cassette for the selectable marker neomycin phosphotransferase typeII gene (nptII) [P-35S/NPTII/NOS3'] and a unique NotI site for cloning the gene of interest. The final vector (pMON13925) was constructed so that the gene of interest and the selectable marker gene were cloned in the same orientation. A vector fragment containing the expression cassettes for these gene sequences could be excised from the bacterial selector (Kan) and ori, gel purified, and used for plant transformation.

Figure 6:
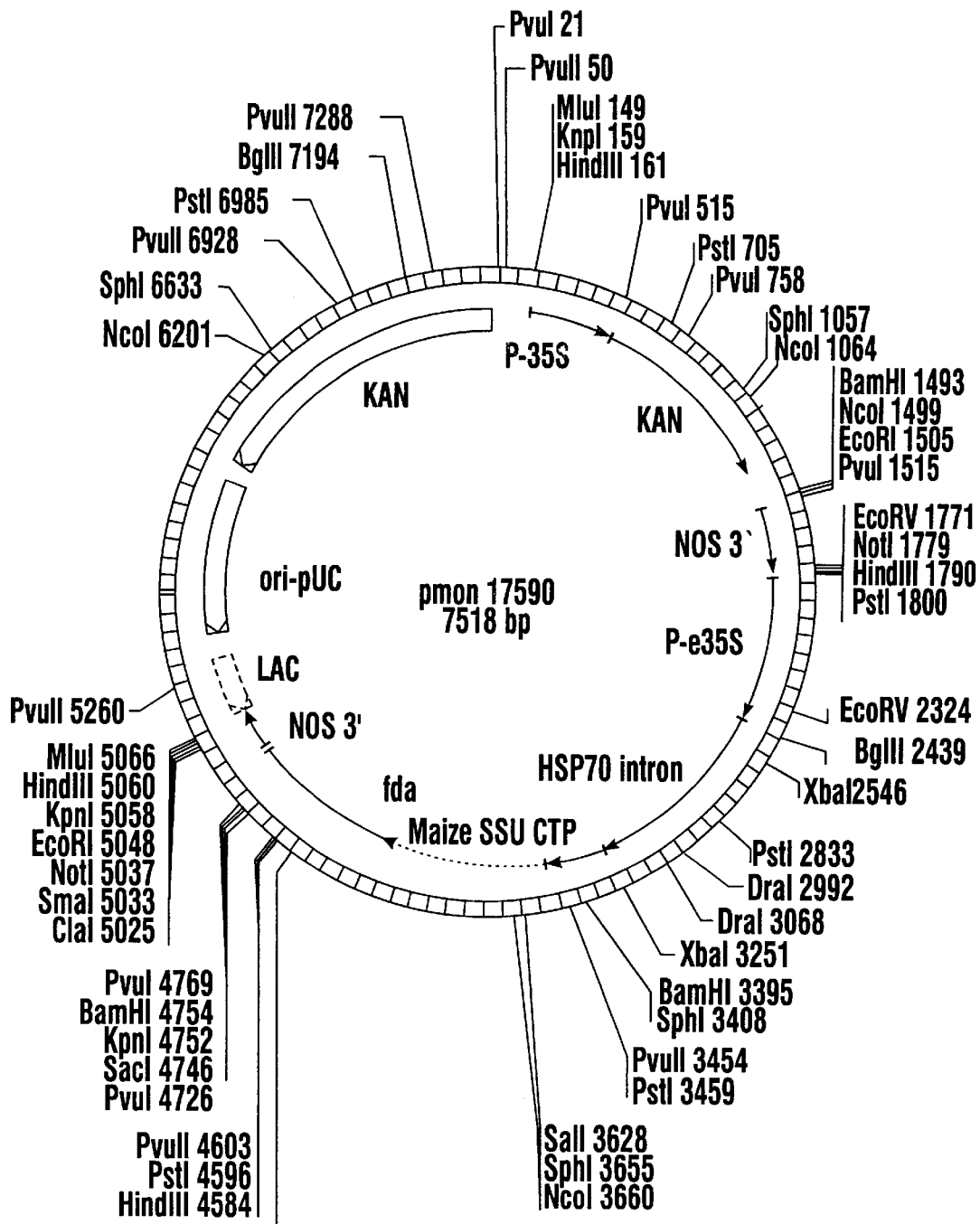
FIG. 6 shows a plasmid map for plant transformation vector pMON17590.

For the chloroplast-targeted expression of the fda gene in corn plants, a construct was made in which the fda gene sequence, coupled to the maize RUBISCO small subunit CTP (Russell et al., 1993), was fused to the backbone of a vector containing the enhanced (CaMV) 35S promoter, the HSP70 intron, and the NOS3' polyadenylation sequences. This created a NotI cassette [P-e35S/HSP70 intron/mzSSuCTP/fda/NOS3'] that was cloned into the NotI site (in the same orientation as the selectable marker cassette [P-35S/NPTII/NOS3']) of the monocot transformation vector pMON30460, to form the vector pMON17590, as shown in FIG. 6. From this vector a fragment containing the fda gene expression cassette and the selectable marker cassette could be excised from the bacterial selector (Kan) and ori, gel purified, and used for plant transformation.

Figure 7:
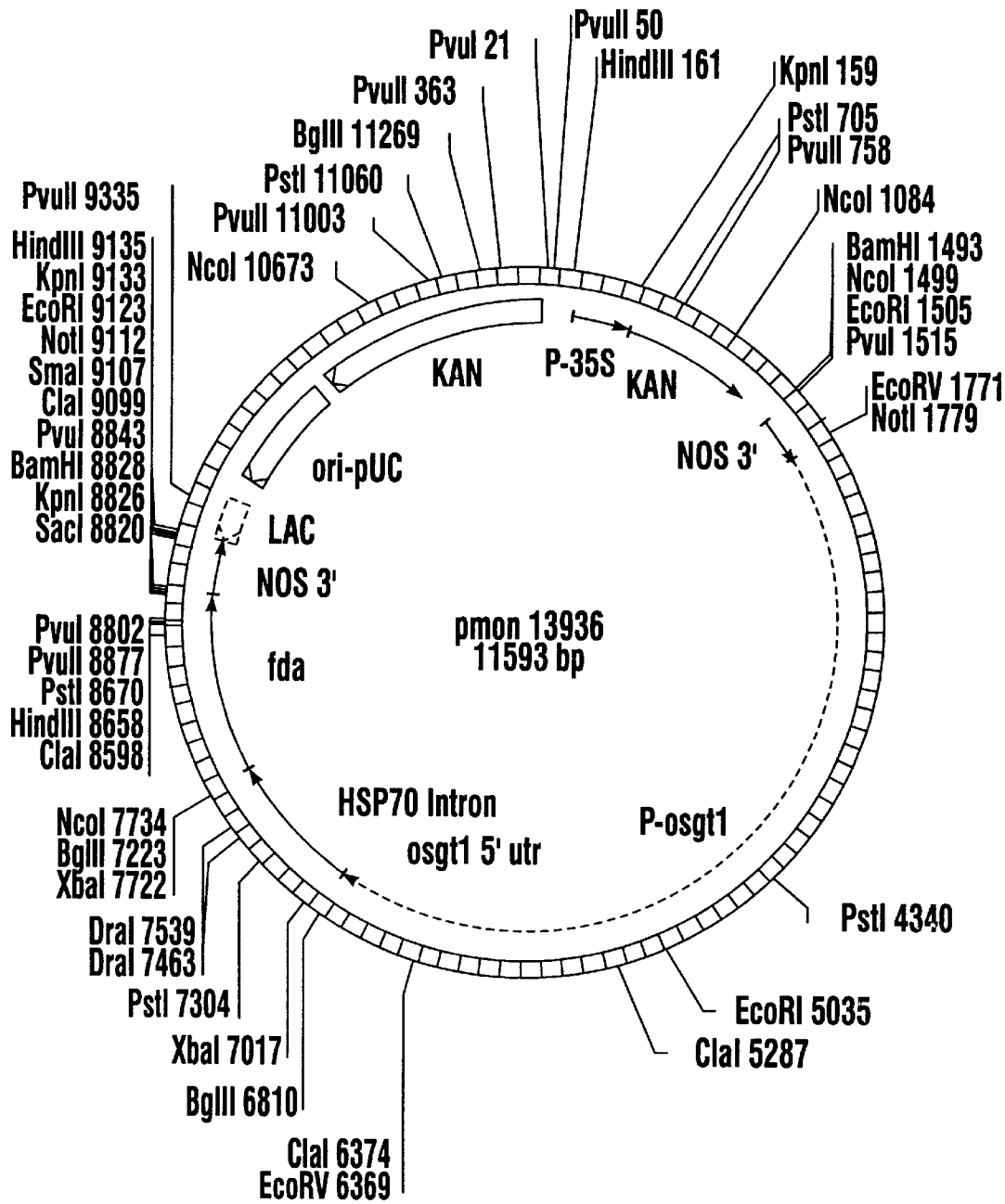
FIG. 7 shows a plasmid map for plant transformation vector pMON13936.

For the cytosolic endosperm-specific expression of the aldolase gene in corn, the fda gene sequence was cloned into a vector (in the same orientation as the selectable marker cassette[P-35S/NPTII/NOS3']) containing the glutelin gene promoter P-osgt1 (Zheng et al., 1993), the HSP70 intron, and the NOS3' polyadenylation sequences to form the vector pMON13936, as shown in FIG. 7. From this vector a fragment containing the fda gene expression cassette [P-osgt1/HSP70intron/fda/NOS3'] and the selectable marker cassette could be excised from the bacterial selector (Kan) and ori, gel purified, and used for plant transformation.

Maize Plant Transformation

Transgenic maize plants transformed with the vectors pMON13925 (described above) or pMON17590 (described above) were produced using microprojectile bombardment, a procedure well-known to the art (Fromm, 1990; Gordon-Kamm et al., 1990; Walters et al., 1992). Embryogenic callus initiated from immature maize embryos was used as a target tissue. Plasmid DNA at 1 mg/mL in TE buffer was precipitated onto M10 tungsten particles using a calcium chloride/spermidine procedure, essentially as described by Klein et al. (1988). In addition to the gene of interest, the plasmids also contained the neomycin phosphotransferase II gene (nptII) driven by the 35S promoter from Cauliflower Mosaic Virus. The embryogenic callus target tissue was pretreated on culture medium osmotically buffered with 0.2M mannitol plus 0.2M sorbitol for approximately four hours prior to bombardment (Vain et al., 1993). Tissue was bombarded two times with the DNA-coated tungsten particles using the gunpowder version of the BioRad Particle Delivery System (PDS) 1000 device. Approximately 16 hours following bombardment, the tissue was subcultured onto a medium of the same composition except that it contained no mannitol or sorbitol, and it contained an appropriate aminoglycoside antibiotic, such as G418", to select for those cells that contained and expressed the 35S/nptII gene. Actively growing tissue sectors were transferred to fresh selective medium approximately every 3 weeks. About 3 months after bombardment, plants were regenerated from surviving embryogenic callus essentially as described by Duncan and Widholm (1988).

Aldolase Activity from Transgenic Maize

In order to measure leaf aldolase activity, corn leaf samples were taken and immediately frozen on dry ice. Aldolase enzyme was extracted from the leaf tissue by grinding the leaf tissue at 4° C. in 1.2 mL of the extraction buffer (100 mM Hepes, pH 8.0, 5 mM $MgCl_2$, 5 mM $MnCl_2$, 100 mM KCl, 10 mM DTT, 1% BSA, 1 mM PMSF, 10 $\mu$g/mL leupeptin, 10 $\mu$g/mL aprotinin). The extract was centrifuged at 15,000× g, at 4° C. for 3 minutes, and the non-desalted supernatant was assayed for enzyme activity. This extraction method gave about 60% recovery of E. coli FDA activity.

Total aldolase activity was determined in 0.98 mL of reaction mixture that consisted of 100 mM EPPS-NaOH, pH 8.5, 1 mM fructose-bisphosphate, 0.1 mM NADH, 5 mM $MgCl_2$, 4 units of alpha-glycerophosphate dehydrogenase, and 15 units of triosephosphate isomerase. The reaction was initiated by addition of 20 $\mu$L of leaf extract. The resulting data, generated from a single experiment, are presented in Table 5.

TABLE 5

Aldolase Activity from Transgenic Maize Leaves

| Lines | A340/min/20 $\mu$L | Activity % |
|---|---|---|
| H99 (control) | 0.113 | 100 |
| pMON 17590 | 0.233 | 206 |
| pMON 13925 | 0.251 | 222 |

A phenotype was visible in the primary transformants (RO plants) expressing the E. coli FDA when the protein was targeted to the chloroplast. The leaves were chlorotic but seed set was normal. R1 plants were grown in both field and in greenhouse experiments. Starch was not detectable in the leaves using an iodine staining and pollination was delayed. It is believed that the phenotype in these corn plants may be the result of the promoter (e35S) used in both the pMON17590 and pMON13925 vectors not being preferred for causing FDA expression in corn. Because e35S is believed to cause mesophyll enhanced expression and the Calvin Cycle in a C4 plant such as corn occurs predominantly in the bundle sheath cells, the use of a promoter directing enhanced expression in the bundle sheath cells (such as the ssRUBISCO promoter) may be preferred. Vectors containing such a promoter and driving expression of FDA have been prepared and are being tested in maize.

In particular, the maize RuBISCO small subunit (PmzSSU, a bundle sheath cell-specific promoter) has been used to construct vectors for cell-specific fda expression in maize. A class I aldolase (fdaI), an fda without an iron sulfur cluster and with different properties from fdaII, was utilized to improve carbon metabolism in C4 crops (e.g. maize). The gene for the class I aldolase was amplified from the genome of Staphylococcus aureus and activity was comfirmed. Transformation vectors were then constructed to express both classes of aldolase (fdaI and fdaII) in a cell-specific manner in maize. The following cassettes have been made:
pMON13899: PmzSSU/hsp70/mzSSU CTP/fdaI
pMON13990PmzSSU/hsp70/mzSSU CTP/fdaII
pMON13988:P35S/hsp70/fdaI.

These vectors were used for corn transformation as described generally above. The biochemical and physiological analysis of the primary transformants should allow for the identification of aldolase gene overexpression that will lead to increase growth and development and yield in maize.

Also, two vectors were used for transformation of corn which would target the expression of the E. coli fda II gene in the maize endosperm. The vector pMON 13936 uses the rice gt1 promoter to drive expression of aldolase in the cytoplasm of the endosperm cells. Another vector (pMON 36416) uses the same promoter with the maize RuBISCO small subunit transit peptide to localize the protein in the amyloplasts. Homozygous lines of the cytosolic aldolase transformants have been identified (Homozygosity of 37 plants was confirmed using western blot analysis) and seed from these plants were collected for grain composition analysis (moisture, protein, starch, and oil). Of the 53 pMON 36416 primary transformants screened for amylopast-targeted aldolase expression, 11 were positive.

These plants will be tested for homozygosity selection/ propagation and kernels from the homozygotes will be used for composition analysis.

Example 4

Plant Transformation and fda Expression in Potato Plants

Targeting of fda Expression

The plant expression vector, pMON17542 (described earlier), in which the fda gene is expressed behind the FMV promoter and the aldolase enzyme is fused to the chloroplast transit peptide CTP2, was used for Agrobacterium-mediated potato transformation.

Figure 8:
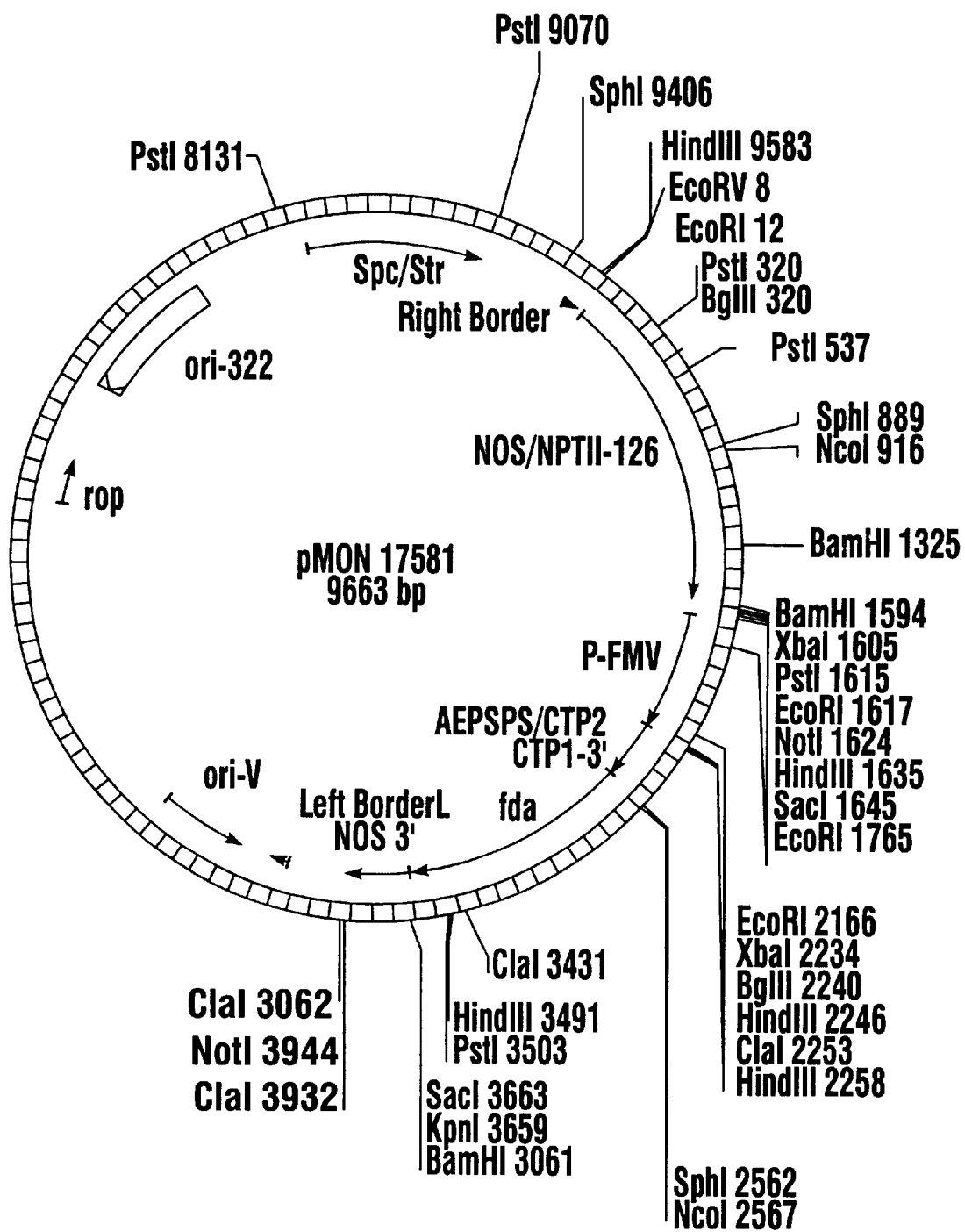
FIG. 8 shows a plasmid map for plant transformation vector pMON17581.

A second potato transformation vector was constructed by cloning the NotI cassette [P-FMV/CTP2/fda/NOS3'] (described earlier) into the unique NotI site of pMON23616. pMON23616 is a potato transformation vector containing the nopaline-type T-DNA right border region (Fraley et al., 1985), an expression cassette for the neomycin phosphotransferase typeII gene [P-35S/NPTII/NOS3'] (selectable marker), a unique NotI site for cloning the gene expression cassette of interest, and the T-DNA left border region (Barker et al., 1983). Cloning of the NotI cassette [P-FMV/ CTP2/fda/NOS3'] (described earlier) into the NotI site of pMON23616 results in the potato transformation vector pMON17581, as shown in FIG. 8. The vector pMON17581 was constructed such that the gene of interest and the selectable marker gene were transcribed in the same direction.

Potato Plant Transformation

The plant transformation vectors were mobilized into the ABI Agrobacterium strain. Mating of the plant vector into the ABI strain was done by the triparental conjugation system using the helper plasmid pRK2013 (Ditta et al., 1980). The vector pMON17542 was used for potato transformation via Agrobacterium transformation of Russet Burbank potato callus, following the method described in PCT Publication WO 96/03513 for glyphosate selection of transformed lines.

After transformation with the vector pMON17542, transgenic potato plantlets that came through selection on glyphosate were screened for expression of E. coli aldolase by leaf Western blot analysis. Out of 112 independent lines assayed, 50 fda-expressing lines (45%) were identified, with fda expression levels ranging between 0.12% and 1.2% of total extractable protein.

The plant transformation vector PMON17581 was used for Agrobacterium-mediated transformation of HS31-638 potato callus. HS31-638 is a Russet Burbank potato line previously transformed with the mutant ADPglucose pyrophosphorylase (glgC16) gene from E. coli (U.S. Pat. No. 5,498,830). The potato callus was transformed following the method described in PCT Publication WO 96/03513, substituting kanamycin (administered at a concentration of 150–200 mg/L) for glyphosate as a selective agent.

The transgenic potato plants were screened for expression of the fda gene by assaying leaf punches from tissue culture plantlets. Western blot analysis (using antibodies raised against the E. coli aldolase) of leaf tissue from the pMON17581-transformed lines identified 12 expressing lines out of 56 lines screened. Expression was detected of a protein migrating at approximately 40 kDa, which is the molecular weight of the E. coli (classII) aldolase subunit and the size of the protein observed after overexpression of the aldolase in E. coli.

Specific Gravity Measurements of Transgenic Potato Plants

From the 50 fda-expressing potato lines obtained after transformation with pMON17542, 7 of the highest expressing lines were micropropagated in tissue culture, and 8 copies of each line were planted in pots 14 inches in diameter and 12 inches deep, containing a mixture of: ½ Metro 350 potting media, ¼ fine sand, ¼ Ready Earth potting media. Wild-type Russet Burbank plantlets from tissue culture were planted as controls. All plants were cultivated for approximately 5 months in the greenhouse in which daytime temperature was approximately 21–23° C. while nighttime temperature was approximately 13° C. Plants were watered every other day throughout their active growing period and fertilized with Peter's 20—20—20 commercial fertilizer once a week, at levels similar to commercial applications. Fertilization was carried out only for the first 2½ months, at which point fertilization was stopped completely. Plants were allowed to naturally senesce, and at approximately 50% senescence, tubers were harvested.

For each line at harvest, all tubers from all 8 pots were pooled and a total weight was obtained. Then for each line, tubers 30 g or greater were pooled and specific gravity was determined on this group of tubers. Specific gravity is the weight of the tubers in air divided by the weight in air minus the weight in water. Results of these weight measurements are presented in Table 6.

TABLE 6

Specific gravity measurements from transgenic potato plants

| Line # | Total Weight | Overall % Yield Increase | Combined Weight of Tubers over 30 g | % Increase in Total Weight (Tubers over 30 g) | Combined Weight of Tubers over 30 g (% of Total Weight) | Specific Gravity |
|---|---|---|---|---|---|---|
| RB | 6609 | | 4477 | | 67.70% | 1.087 |
| 40652 | 5138 | neg | 1307 | neg | 25.40% | 1.08 |
| 40611 | 7170 | 8.5% | 4533 | 1.3% | 63.20% | 1.083 |
| 40608 | 7470 | 13.0% | 1070 | neg | 14.30% | 1.081 |
| 40632 | 7776 | 21.8% | 5453 | 21.8% | 70.10% | 1.088 |
| 40614 | 8688 | 31.5% | 5468 | 22.2% | 62.90% | 1.083 |
| 40631 | 8800 | 33.2% | 6188 | 38.2% | 70.30% | 1.084 |
| 40610 | 9746 | 47.0% | 7777 | 73.0% | 80% | 1.087 |

This summarizes the tuber yield and specific gravity for all seven lines grown in the greenhouse. The results indicate that, in comparison to the control, all but one of the fda lines show an increase in overall tuber yield, and that in four lines, there is a corresponding increase in percentage of tubers that weigh more than 30 g. For combined tubers over 30 g, the percent of total weight is near that of the control, and for two lines is greater than the control. This indicates that five out of the six of the lines show higher overall yield and are not making smaller tubers. In other words, with the increase in overall yield, there is a corresponding increase in percentage of bigger tubers (over 30 g). However, there is no increase in specific gravity of the tubers.

In conclusion, it appears that expression of fda in potato produces greater numbers of tubes per plant without a sacrifice in tuber size. This represents a yield benefit in that the farmer could potentially be able to produce the same amount of tubers using less acreage. Similar experiments will also be performed by co-expression of fda with other carbohydrate metabolizing genes, such as glgC16, in order to determine how such combinations will affect tuber yield, tuber solids deposition and overall tuber specific gravity.

Aldolase Activity from Transgenic Potato

After being cultivated for 3 months (post planting) in the greenhouse, leaf samples were taken from 6 of the highest fda-expressing potato lines, obtained after transformation with pMON17542, and assayed for aldolase activity.

In order to measure potato leaf aldolase activity, duplicate leaf samples from each line were taken and immediately frozen on dry ice. Aldolase was extracted from 0.2 g of leaf tissue by grinding at 4° C. in 1.2 mL of the extraction buffer: 100 mM Hepes, pH 8.0, 5 mM $MgCl_2$, 5 mM $MnCl_2$, 100 mM KCl, 10 mM DTT, 1% BSA, 1 mM PMSF, 10 µg/mL leupeptin, 10 µg/mL aprotinin. The extract was assayed for aldolase activity as described earlier.

Six independent transgenic potato lines expressing fda were tested for aldolase activity. The expression of fda in leaves is an indicator of the expression in the whole plant because the FMV promoter used to drive expression of the respective encoding DNAs directs gene expression constitutively in most, if not all, tissues of potato plants.

Table 7 summarizes the quantitative protein expression data for each of the lines, and the percent activity for each individual line.

TABLE 7

Aldolase Activity from Transgenic Russet Burbank Potato Leaves

| Lines | Exp. #1 | | Exp. #2 | | Average |
|---|---|---|---|---|---|
| | Act (U/gFW) | % Act | Act (U/gFW) | % Act | % Activity |
| Control | 4.461 | 100 | 4.732 | 100 | 100 |
| 40608 | 6.969 | 156 | 8.055 | 170 | 163 |
| 40610 | 8.489 | 190 | 7.326 | 155 | 173 |
| 40652 | 5.812 | 130 | 6.367 | 135 | 132 |
| 40632 | 5.257 | 118 | 4.244 | 90 | 104 |
| 40631 | 5.764 | 129 | 4.968 | 105 | 117 |
| 40611 | 5.715 | 128 | 5.836 | 123 | 126 |

Solids Uniformity in Transgenic Potato

Twenty-five Russet Burbank lines expressing fda (potato lines designated "Maestro"), obtained after transformation with pMON17542, and fifteen Russet Burbank Simple Solid lines, also containing glgC16 (PCT Publication WO 91/19806 and U.S. Pat. No. 5,498,830), expressing fda (potato lines designated "Segal"), obtained after transformation with pMON17581, were field tested at two different sites. For each field site, 36 plants per line (three repetitions of 12 plants per line) were evaluated for tuber solids distribution. At harvest, tubers were pre-sorted at each field site into a ten to twelve ounce category, and nine tubers from each replicated plot were analyzed in groups of three.

For a typical 10–12 ounce tuber having a diameter of 7–8 cm, starch distribution was evaluated by removing the center longitudinal slice (13 mm) from each tuber. Slices were then peeled and laid flat on a cutting board where the inner tuber region (pith region) was removed by a 14-mm cork punch. The tissue from pith to cortex (perimedullary region) was removed by an up-to-a 2-inch cork punch. The remaining cortex tissue was approximately an 8-mm wide ring from the outermost region of the slice.

Specific gravity was then determined by weighing both the pooled pith punches and pooled cortex punches in air and then in water:

Specific gravity=Air $Wt./$(Air $Wt.$–Water $Wt.$)

After calculating specific gravity, solids levels were determined by the following equation:

−214.9206+(218.1852*Sp. Gravity)

The degree of solids uniformity (Solids Uniformity Index) is determined by calculating the pith to cortex solids ratio (pith solids divided by cortex solids). The three groups of three tubers per plot were averaged, at which point the average of three plot replications was calculated per field site.

Analyses of several previous solids uniformity field trials (data not shown) have demonstrated nontransgenic, wild-type Russet Burbank potato to have a typical pith to cortex tuber solids ratio within the range of 68% to 72%, depending on growing region and agricultural practices. Tables 8–11 provide the pith to cortex solids ratios by plant line number, with a higher pith to cortex solids ratio indicating a greater degree of solids uniformity.

Tables 8 and 9 represent the data from one field site (site 1) for Segal and Maestro, respectively, and illustrate that the majority of Segal and Maestro lines have higher pith to cortex solids ratios than that of 68.4% for the Russet Burbank control, with some lines approaching an 82% pith to cortex solids ratio.

Tables 10 and 11 represent the data from another field site (site 2) for Segal and Maestro, respectively, and also illustrate that the majority of Maestro and Segal lines have higher pith to cortex solids ratios than that of the Russet Burbank control, with some lines approaching an 88% pith to cortex solids ratio. In the site 2 field trial, the Russet Burbank control had an a typical, abnormally high pith-to-cortex solids uniformity ratio of 79.3%, which was most likely due to environmental growing conditions. The site 2 results demonstrate that expression in Russet Burbank potato of *E. coli* fda, alone or with co-expression of glgC16, increases tuber solids uniformity even in a growing season when tuber solids uniformity is already extremely high in nontransgenic Russet Burbank. That is, the fda gene continues to perform when agricultural conditions are already conducive to an abnormally high solids uniformity level.

TABLE 8

Solids Uniformity Index: Pith Solids to Cortex Solids Ratio. Segal Russet Burbank Lines. Site 1

| Line | Ratio |
|---|---|
| S-29 | 79.1 |
| S-9 | 75.8 |
| S-20 | 71.3 |
| S-15 | 71.3 |
| S-21 | 70.5 |
| S-5 | 70.2 |
| S-18 | 70.0 |
| RB control | 68.4 |
| S-32 | 68.3 |
| S-16 | 65.6 |

TABLE 9

Solids Uniformity Index: Pith Solids to Cortex Solids Ratio.
Maestro Russet Burbank Lines. Site 1

| Line | Ratio |
|---|---|
| M-13 | 74.0 |
| M-12 | 73.6 |
| M-1 | 73.4 |
| M-3 | 73.0 |
| M-6 | 72.4 |
| M-9 | 71.2 |
| M-11 | 70.6 |
| M-18 | 70.5 |
| M-17 | 69.9 |
| M-19 | 69.4 |
| M-5 | 69.3 |
| M-20 | 68.9 |
| RB control | 68.4 |
| M-8 | 68.3 |
| M-43 | 67.7 |
| M-23 | 67.3 |
| M-7 | 67.0 |
| M-39 | 66.6 |
| M-22 | 66.0 |
| M-10 | 65.4 |
| M-27 | 61.4 |

TABLE 10

Solids Uniformity Index: Pith Solids to Cortex Solids Ratio
Segal Russet Burbank Lines. Site 2

| Line | Ratio |
|---|---|
| S-33 | 87.4 |
| S-54 | 87.1 |
| S-05 | 86.8 |
| S-29 | 85.1 |
| S-21 | 84.3 |
| S-16 | 83.2 |
| S-20 | 81.5 |
| S-18 | 80.7 |
| S-32 | 80.6 |
| RB control | 79.3 |
| S-09 | 79.0 |

TABLE 11

Solids Uniformity Index: Pith Solids to Cortex Solids Ratio
Maestro Russet Burbank Lines. Site 2

| Line | Ratio |
|---|---|
| M-04 | 87.7 |
| M-18 | 83.9 |
| M-17 | 83.8 |
| M-03 | 83.7 |
| M-09 | 83.4 |
| M-15 | 83.2 |
| M-29 | 82.9 |
| M-44 | 82.3 |
| M-08 | 82.2 |
| M-43 | 81.6 |
| M-22 | 81.1 |
| M-05 | 80.8 |
| M-01 | 80.5 |
| M-20 | 80.2 |
| M-45 | 79.6 |
| M-39 | 79.5 |
| M-27 | 79.5 |
| RB control | 79.3 |
| M-13 | 78.9 |
| M-22 | 78.8 |
| M-19 | 78.7 |

TABLE 11-continued

Solids Uniformity Index: Pith Solids to Cortex Solids Ratio
Maestro Russet Burbank Lines. Site 2

| Line | Ratio |
|---|---|
| M-07 | 78.2 |
| M-12 | 77.9 |
| M-23 | 77.3 |
| M-06 | 76.5 |
| M-10 | 75.0 |
| M-11 | 74.1 |

Figure 9:
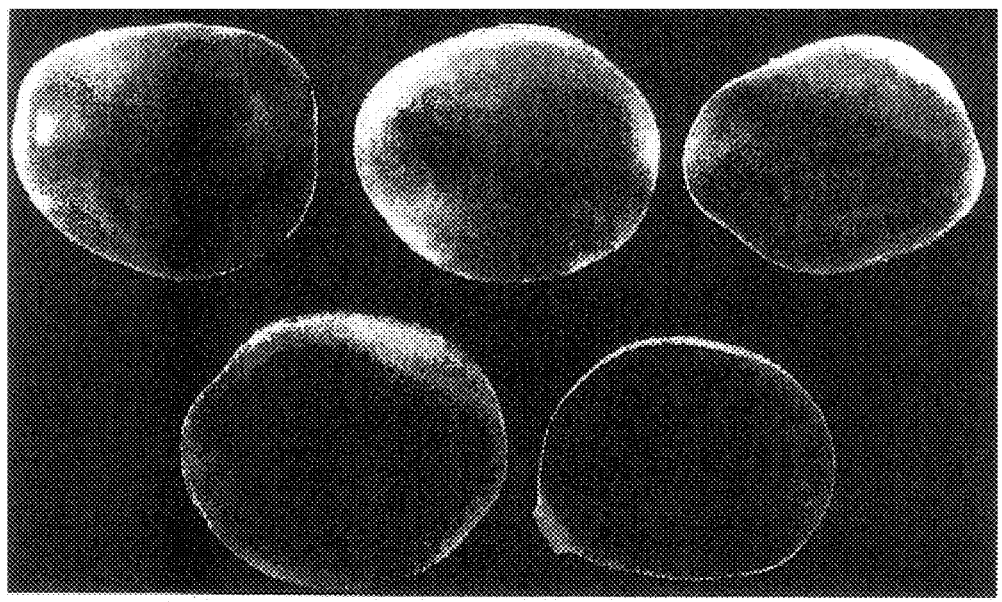
FIG. 9 shows potato tuber cross-sections of improved solids uniformity Segal Russet Burbank lines (top row) versus unimproved nontransgenic Russet Burbank (bottom row).

The effect of aldolase on pith to cortex solids ratios in the Segal lines is slightly more dramatic than in Maestro lines. We believe this phenotype is due to expression of fda in a background in which the Russet Burbank host expresses glgC16 at a relatively low to moderate level, and that the combination of fda plus glgC16 provides improved benefits. Cross sectional tuber slices (FIG. 9) of three Segal lines with improved solids uniformity illustrate a greater deposition of starch within the inner regions of the tuber. Specifically, an increase in cortex volume accompanied by relocation of the xylem ring towards the center of the tuber, plus a more opaque pith tissue due to an increase in starch density, are evident in the transgenic lines. This physiological alteration may be due to an increase in sucrose translocation from source to sink, which may influence phloem element distribution during tuber development or sucrose availability for starch biosynthesis across the tuber.

Example 5

Plant Transformation and FDA Expression in Cotton Plants

The *E. coli* fda vectors pMON 17524 [FMV/CTP1/fda] (FIG. 2) and pMON 17542 [FMV/CTP2/fda] (FIG. 3) were transformed into cotton using Agrobacterium as described by Umbeck et al. (1987) and in U.S. Pat. No. 5,004,863. The protein was targeted to the chloroplast using either the Arabidopsis SSU CTP 1 (pMON17524) or the Arabidopsis EPSPS (pMON17542) chloroplast transit peptide.

Aldolase Expression in Cotton

Five-week-old calli transformed with both vectors were analyzed by Western blot analyses and by aldolase assays. Western blot analysis indicated a large amount of protein at the position of the full-length FDA standard and a lesser amount at the same position in the control callus extracts. It appeared that the protein was fully processed. To verify that FDA was expressed in the tissue and for comparison of activity, calli transformed with the two vectors were extracted in a buffer that would prevent loss of activity of the transgene product. BSA was added to final concentration of 1 mg/mL, which limited the analysis of processing on import by Western blot. Aldolase assays were performed plus or minus 25 mM EDTA, which inhibits the *E. coli* enzyme but not the plant enzyme. The results of the assays are shown in Table 12.

TABLE 12

Aldolase Activity in Cotton Calli and Cotton Leaf

| | $\Delta A340\ e^{-3}$/mg protein/5 min | | |
|---|---|---|---|
| | Colony# | −EDTA | +EDTA | Fold Increase |
| Controls | | | | |
| Cotton Leaf (Coker) | | 4.0 | 4.2 | — |
| Uninoculated Calli | | 7.7 | 5.6 | 1.3X |

TABLE 12-continued

Aldolase Activity in Cotton Calli and Cotton Leaf

| | | $\Delta A340\ e^{-3}$/mg protein/5 min | | |
|---|---|---|---|---|
| | Colony# | −EDTA | +EDTA | Fold Increase |
| Inoculated Calli (E35S/ GUS) FDA calli | #1 #2 | 6.8 3.5 | 6.1 4.0 | — — |
| pMON 17542 | #1 #3 #5 #4 | 3.5 5.5 9.2 19.8 | 2.3 2.6 3.8 3.6 | 1.5X 2.1X 2.4X 5.5X |
| pMON17524 | #2 #3 #5 #6 | 15.2 12.5 14.4 4.1 | 5.8 4.0 2.9 1.2 | 2.6X 3.1X 4.9X 3.5X |

The results indicate that there is good expression of the fda gene in cotton callus. Almost all calli had at least twofold higher aldolase activity, and the increase was sensitive to inhibition by EDTA. Processing appeared complete by Western blot analysis using these samples.

REFERENCES CITED

Alefounder et al. (1989) *Biochem. J.* 257:529–534
Ammirato et al. (1984) *Handbook of Plant Cell Culture—Crop Species.* Macmillan Publ. Co.
Bai et al. (1975) *Arch. Biochem. Biophys.* 168: 230–234.
Baldwin et al. (1978) *Biochem. J.* 169: 633–641
Barker et al. (1983) Plant Mol Biol 2 (6): 335–350.
Benfey et al. (1989) *EMBO J*, 5: 2195–2202.
Besmond et al. (1983) *Biochem. Biophys. Res. Commun.* 117, 601–609.
Bevan (1984) *Nucleic Acids Res.* 12 (22): 8711–8721.
Bevan et al. (1986) *Nucleic Acids Res.* 14 (11):4625–4638.
Campbell et al. (1994) *Canadian Journal of Forest Research* 24 (8):1689–1693.
Cerdan et al. (1997) *Plant Molecular Biology* 33 (2): p245–255.
Chopra et al. (1990) *Plant Molecular Biology* 15:517–520.
Clayton (1985) *EMBO J.* 4, 2997–3003.
Cremona (1968) *G. Bot. Ital.* 102, 253–259.
Daniell et al. (1998) *Nature Biotechnology* 16:345–348.
Datta et al. (1990) *Bio-technology* 8:736–740.
Ditta et al. (1980) *Proc Natl Acad Sci USA* 77(12): 7347–7351.
Duncan and Widholm (1988) *Plant Cell Reports* 7: 452–455.
Edwards et al. (1990). *Proc Natl Acad Sci USA* 87 (9): p3459–3463.
Fejes et al. (1990). *Plant Mol Biol* 15 (6): p921–932.
Fraley et al. (1983) *Proc Natl Acad Sci USA* 80: 4803–4807.
Fraley et al. (1985) *Bio/Technology* 3 (7): 629–635.
Fromm, M., (1990) UCLA Symposium on Molecular Strategies for Crop Improvement, Apr. 16–22, 1990. Keystone, Colo.
Fromm et al. (1987) *Methods in Enzymology.* 153:351–366.
Gordon-Kamm et al. (1990) *Plant Cell* 2: 603–618.
Gotz et al. (1979) *FEMS Microbiol. Lett.* 5:253–257.
Gowda et al. (1989). *Journal of Cellular Biochemistry supplement* 13D, 301 (Abstract).
Groussol et al. (1986) *Physiologie Vegetale* 24(1):123–134.
Guerrini et al. (1971) *Arch. Biochem. Biophys.* 146, 249–255.
Hannapel (1990) *Plant Physiol.* 94: 919–925.
Hayashimoto et al. (1990) *Plant Physiol.* 93:857–863.
Herrera-Estrella et al. (1983) *Nature* 303:209.
Hinchee et al., *Bio/Technology* 6:915–922 (1988).
Horsch and Klee. (1986) *Proc. Natl. Acad. Sci. U.S.A.* 83:4428–4432.
Jack (1973) Ph.D. Dissertation, University of Cambridge.
Jack and Harris (1971) *Biochem. J.* 124, 680–690.
Jefferson et al. (1990) *Plant Mol. Biol.* 14: 995–1006.
Joh et al. (1986) *J. Mol. Biol.* 190:401–410.
Kay et al. (1987) *Science* 236: 1299–1302.
Klee et al. (1985) *Bio-Technology* 3(7): 637–642.
Klein et al. (1988) *Bio/Technology* 6: 559–563.
Kretsch et al. (1995) *Plant Journal* 7 (5): p715–729.
Lai et al., (1974) *Science* 183, 1204–1206.
Lebherz and Rutter (1973) *J. Biol. Chem.* 248:1650–1659.
Lebherz et al (1984) *J. Biol. Chem.* 259 (2):1011–1017.
Leyva et al. (1995) *Plant Physiology* 108(1):39–46.
London and Kline (1973) *Bacteriol. Rev.* 37:453–478.
Lloyd et al. (1991). *Mol. Gen. Genet.* 225 (2):209–216.
Luan et al. (1992). *Plant Cell* 4 (8):971–981.
Luebberstedt et al. (1994) *Plant Physiology* 104 (3):997–1006.
Maniatis et al. (1982) *Molecular Cloning: A laboratory manual.* Cold Spring Harbor Laboratory Press, Cold Spring Harbor, N.Y.
Matsuoka et al. (1993). *Proc. Natl. Acad. Sci. U.S.A.* 90(20) :9586–9590.
Mignery et al (1988) *Gene* 62:27–44.
Muller et al (1990) *Mol. Gen. Genet.* 224:136–146.
Oelmueller et al. (1992). *Res. Photosynth., Proc. Int. Congr. Photosynth., 9th* Volume 3: p219–24. Editor(s): Murata, Norio. Publisher: Kluwer, Dordrecht, Neth.
Pedersen et al. (1982) *Cell* 29:1015–1026.
Potrykus et al. (1985), *Mol. Gen. Genet.* 199:183–188.
Rocha-Sosa et al. (1989) *EMBO J.* 8 (1):23–29.
Rogers et al. (1987) *Improved vectors for plant transformation: expression cassette vectors and new selectable markers.* In *Methods in Enzymology.* Edited by R. Wu and L. Grossman. p253–277. San Diego: Academic Press.
Rohde et al. (1990) *J. Genet. & Breed.* 44:311–315.
Russell et al. (1993) *Plant Cell Reports* 13:24–27.
Russell and Fromm (1997) *Transgenic Research* 6 (2):157–168.
Russel and Gibbs (1967) *Biochim. Biophys. Acta* 132, 145–154
Salanoubat and Belliard (1987) *Gene* 60:47–56.
Salanoubat and Belliard (1989) *Gene* 84:181–185.
Samac et al. (1990) *Plant Physiol.* 93:907–914.
Sambrook et al. (1989) *Molecular cloning: A laboratory manual,* 2nd ed., Cold Spring Harbor Laboratory Press, Cold Spring Harbor, N.Y.
Schmidhauser and Helinski. (1985) *J. Bacteriol.* 164–155.
Sonnewald et al. (1994) *Plant Cell and Environment* 17:649–658.
Stalker et al. (1988) *J. Biol. Chem.* 263:6310–6314.
Stark et al. (1992) *Science* 258: 287–292.
Stockhaus et al. (1989). *EMBO Journal* 8(9):2445–2451.
Stribling and Perham (1973) *Biochem. J.* 131:833–841.
Suzuki et al. (1994) *Plant Mol. Biol.* 25(3):507–516.
Thillet et al. (1988) *J. Biol. Chem.* 263:12500–12508.
Thompson et al. (1994) *Nucl. Acids Res.* 22:4673–4680.
Tierney et al. (1987) *Planta* 172:356–363.
Truernit et al. (1995) *Planta* 196 (3):564–570.
Tsutsumi et al. (1984) *J. Biol. Chem.* 259, 14572–14575.
Umbeck et al. (1987) *Biotechnology.* 5, 263–266.
Vain et al. (1993) *Plant Cell Reports* 12: 84–88.
Vasil et al. (1990) *Bio/Technology* 8:429–434.

Vasil et al. (1992) *Bio/Technology* 10:667–674.
Walters et al. (1992) *Plant Molecular Biology* 18: 189–200.
Witke and Goetz (1993) *Journal of Bacteriology* 175(22): 7495–7499
Wong et al. (1988) *Gene* 68: 193–203.
Yamamoto et al. (1994) *Plant and Cell Physiology* 35(5):773–778.
Zheng et al. (1993) *Plant J.* 4: 3357–3366.

What is claimed is:

1. In a method for the processing of potatoes into fries or chips, the improvement comprising, utilizing a potato that overexpresses a prokaryotic fructose 1,6 bisphosphate aldolase transgene providing a higher solids uniformity in such potato.

2. The method of claim 1, wherein said potato contains a recombinant, double stranded DNA molecule containing:
   a) a promoter functional in plant cells; and
   b) a DNA sequence coding for a fructose 1,6 biphosphate aldolase and operatively linked to the promoter in sense orientation.

3. The method of claim 1, wherein said potato overexpresses a fructose 1,6 bisphosphate aldolase transgene and exhibits improved yield compared to potatoes not transformed with the transgene.

4. The method of claim 1, wherein the DNA sequence coding for fructose 1,6 bisphosphate aldolase is a sequence which hybridizes with the coding region depicted as SEQ ID NO. 1 under conditions wherein sodium chloride concentrations are about 0.02 M to about 0.15 M and temperatures range from about 50° C. to about 70° C.

5. The method of claim 1, wherein the DNA sequence coding for a fructose 1,6 bisphosphate aldolase has at least about 80% identity with the coding region depicted as SEQ ID NO. 1.

6. The method of claim 1, wherein the DNA sequence coding for a fructose 1,6 bisphosphate aldolase has the coding region depicted as SEQ ID NO. 1, or a nucleotide sequence that encodes the same peptide as SEQ ID NO. 1.

* * * * *